United States Patent [19]
Nakamatsu

[11] Patent Number: 4,987,896
[45] Date of Patent: Jan. 29, 1991

[54] APPARATUS FOR INCREASING THE ACTIVITY OF THE HUMAN BRAIN

[76] Inventor: Yoshiro Nakamatsu, 1-10-309, Minami Aoyama 5-chome, Minato-ku, Tokyo, Japan

[21] Appl. No.: 395,290

[22] Filed: Aug. 17, 1989

Related U.S. Application Data

[63] Continuation of Ser. No. 188,200, Apr. 28, 1988, abandoned, which is a continuation of Ser. No. 608,918, May 10, 1984, abandoned, which is a continuation of Ser. No. 317,205, Nov. 2, 1981, abandoned.

[30] Foreign Application Priority Data

| Mar. 28, 1981 | [JP] | Japan | 56-44719 |
| Jul. 30, 1981 | [JP] | Japan | 56-118455 |
| Aug. 6, 1981 | [JP] | Japan | 56-122393 |
| Aug. 6, 1981 | [JP] | Japan | 56-122394 |
| Aug. 6, 1981 | [JP] | Japan | 56-122395 |
| Aug. 6, 1981 | [JP] | Japan | 56-122396 |

[51] Int. Cl.$^5$ ............................ A61F 7/00
[52] U.S. Cl. ............................ 128/399; 128/402; 128/897
[58] Field of Search ............... 128/399–400, 128/402–3, 380, 382, 897; 165/43, 96; 237/12.3 A, 12.3 B

[56] References Cited

U.S. PATENT DOCUMENTS

| 3,696,814 | 10/1972 | Umemoto | 128/380 |
| 3,916,988 | 11/1975 | Matsuda | 165/96 X |
| 4,002,175 | 1/1977 | Brainard et al. | 128/399 |
| 4,108,376 | 8/1978 | Matsuda et al. | 237/12.3 X |
| 4,109,661 | 8/1978 | Fukuoka | 128/582 |
| 4,172,454 | 10/1979 | Warncke et al. | 128/399 X |
| 4,192,297 | 3/1980 | LaBrecque | 128/66 |
| 4,214,588 | 7/1980 | Byler | 128/403 X |
| 4,330,892 | 5/1982 | Fukushima | 600/15 X |

FOREIGN PATENT DOCUMENTS

| 0652942 | 3/1979 | U.S.S.R. | 128/400 |
| 0760972 | 9/1980 | U.S.S.R. | 128/400 |

OTHER PUBLICATIONS

Consumer Guide 1989 cars, pp. 21–23.

Primary Examiner—Lee S. Cohen
Assistant Examiner—J. P. Lacyle
Attorney, Agent, or Firm—Jordan and Hamburg

[57] ABSTRACT

This invention provides an apparatus for increasing the activity of the human brain which includes a section for cooling the head of a person and another section for warming his feet or legs.

10 Claims, 22 Drawing Sheets

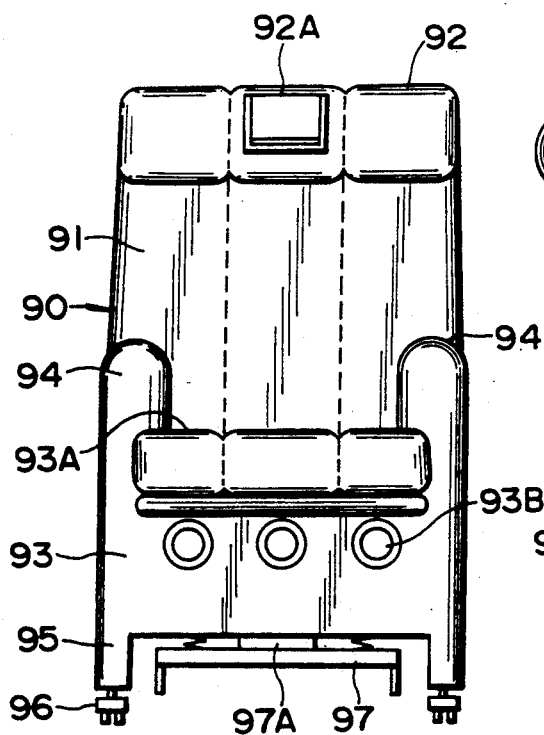
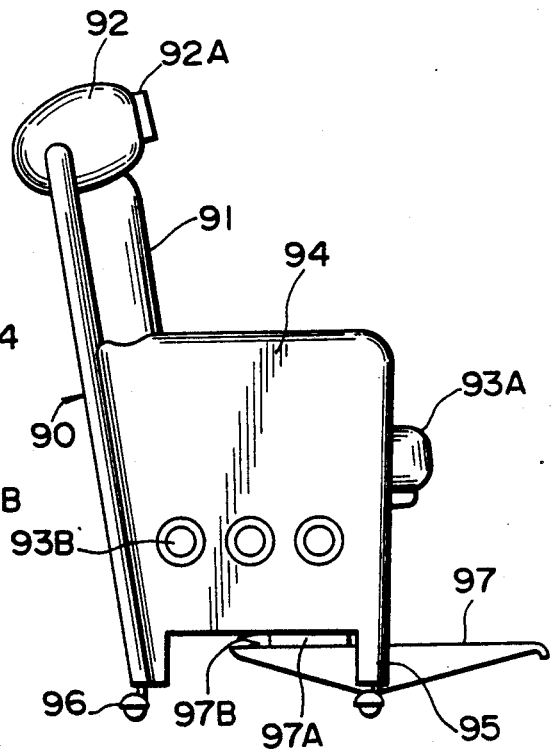
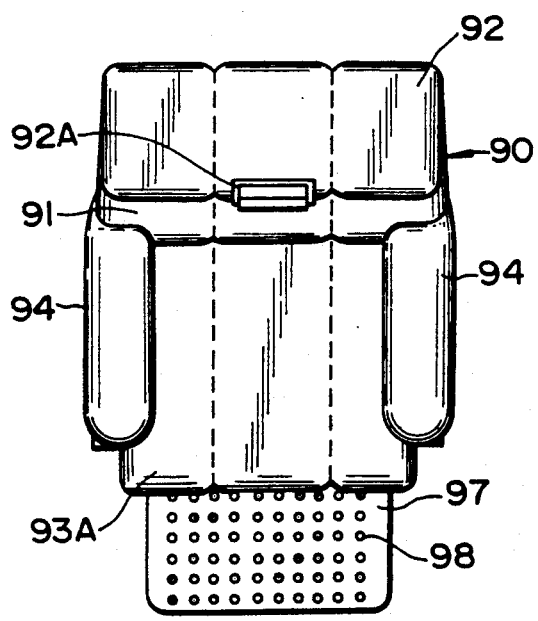
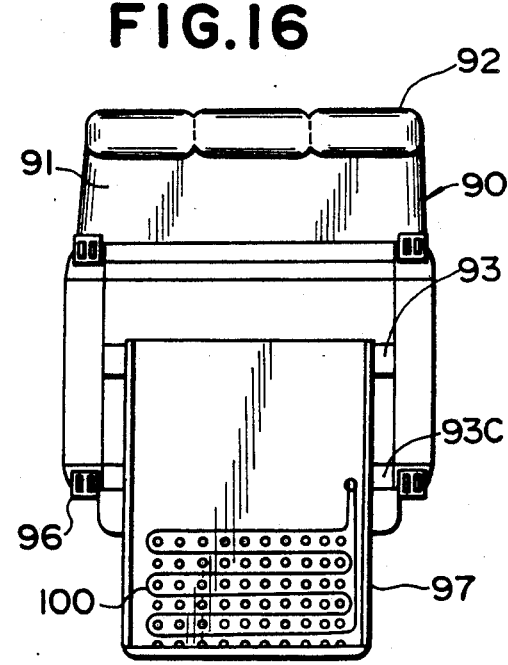

FIG.21
FIG.19
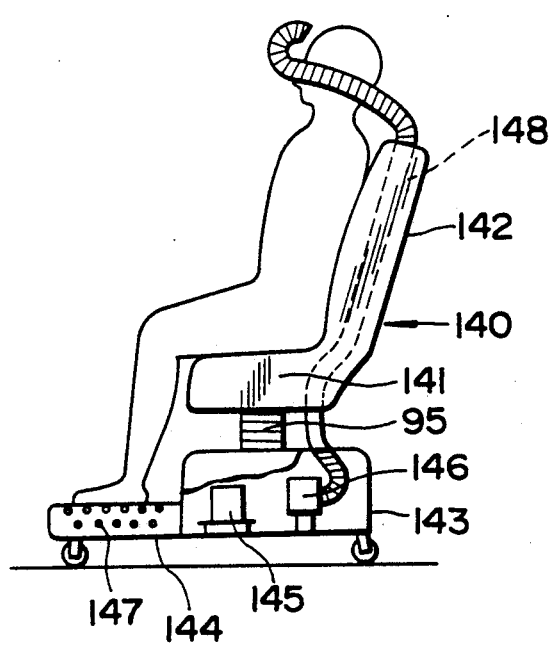
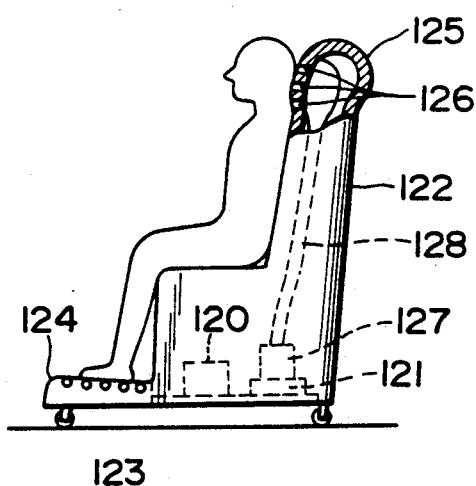
FIG.20
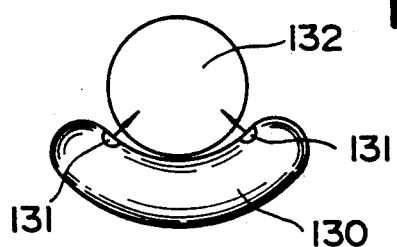
FIG.22
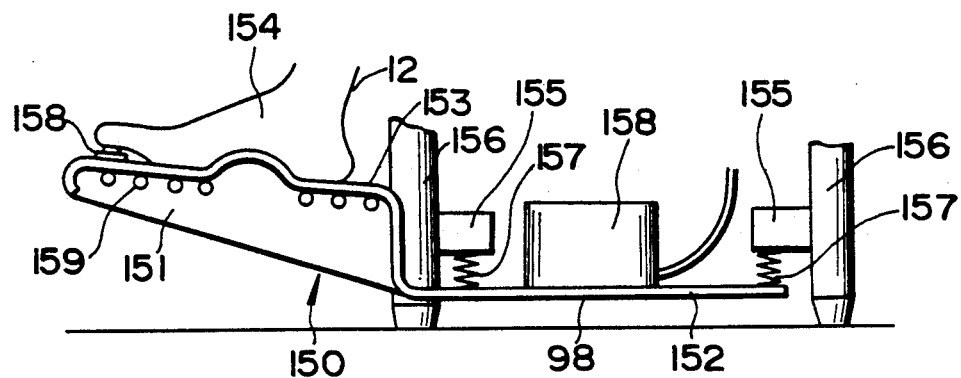

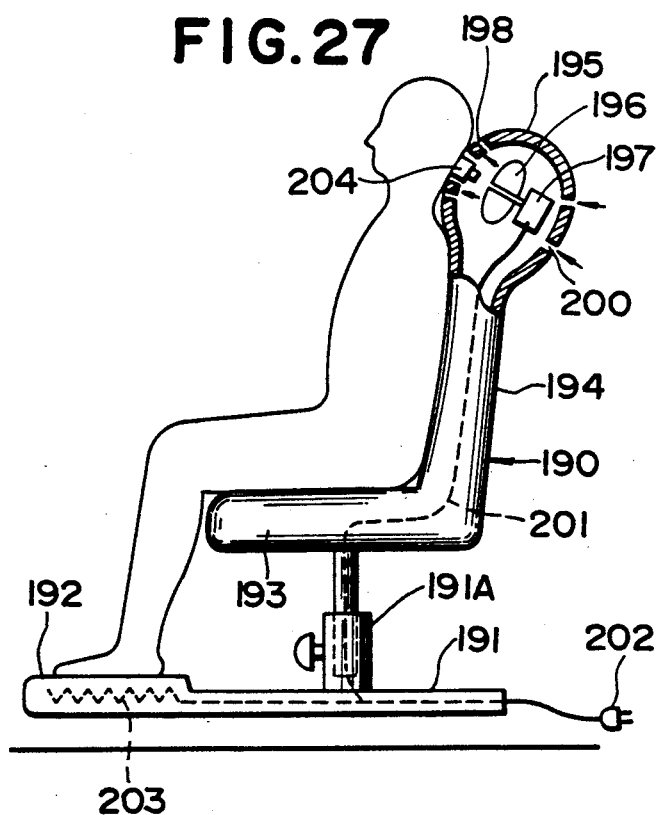
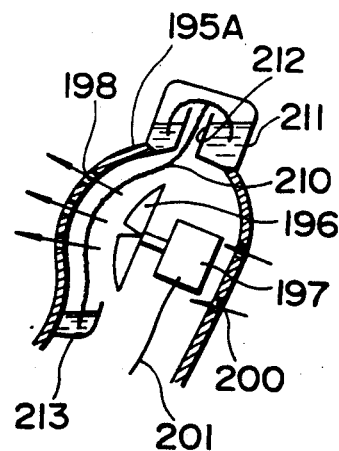
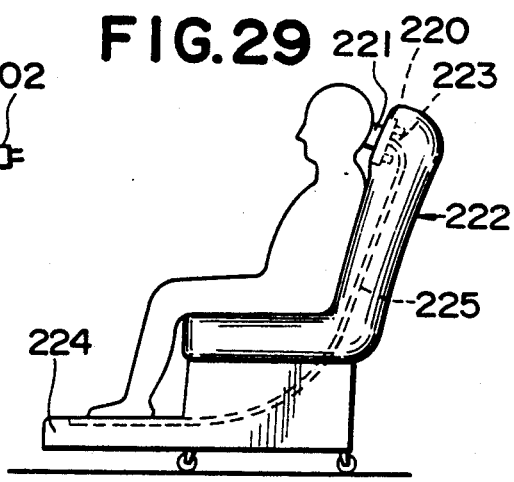
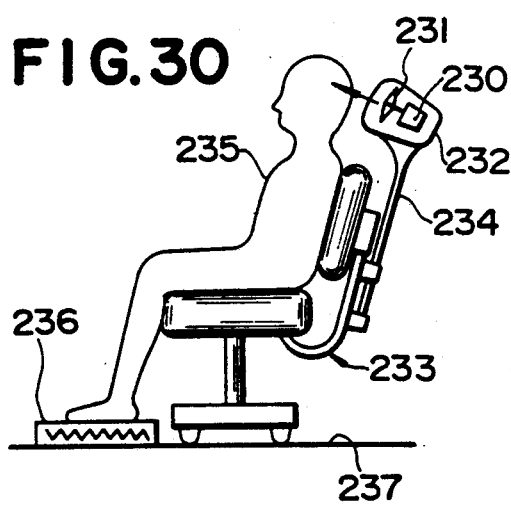
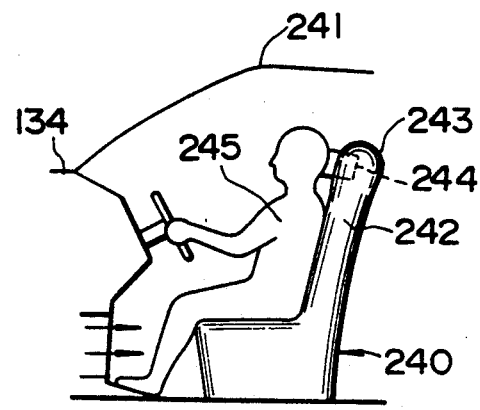

FIG. 42
FIG. 43
FIG. 44
FIG. 45
FIG. 46
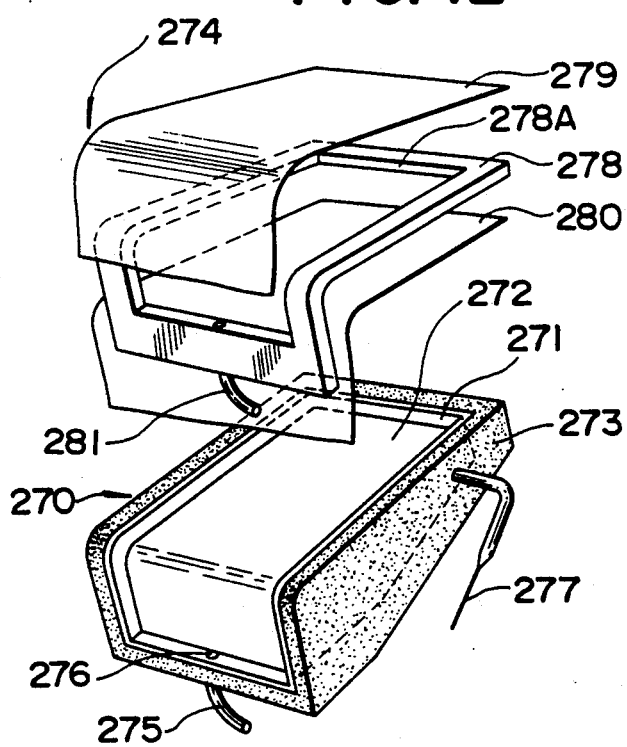
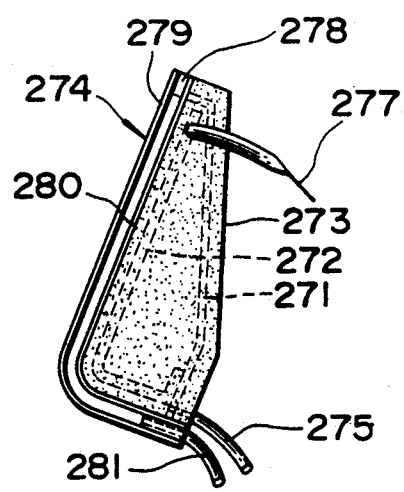
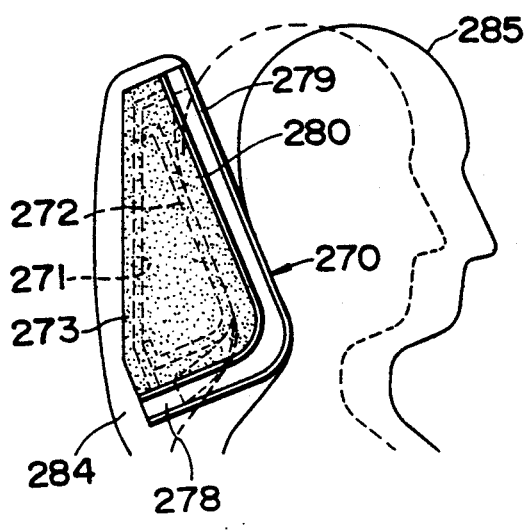
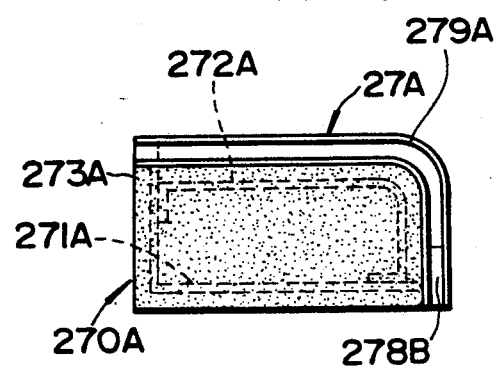
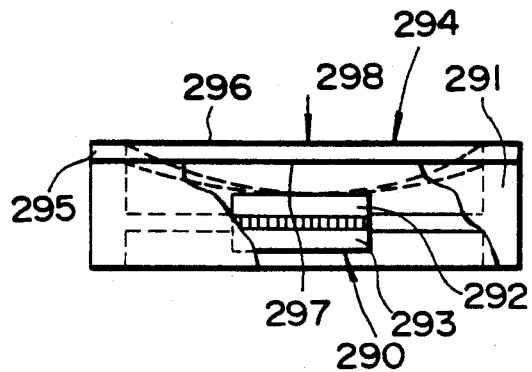

FIG.67
FIG.68
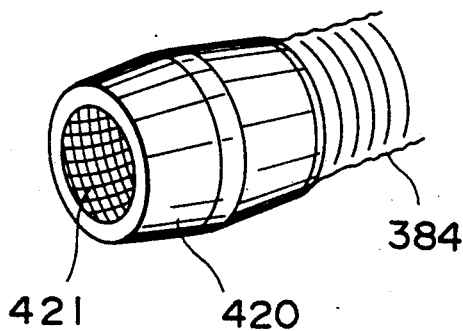
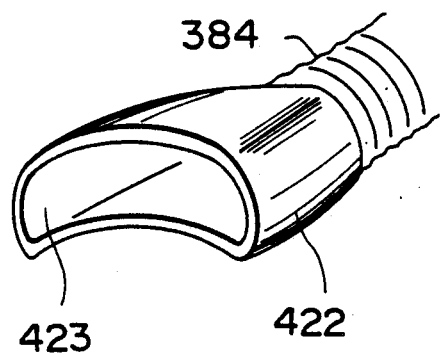
FIG.69
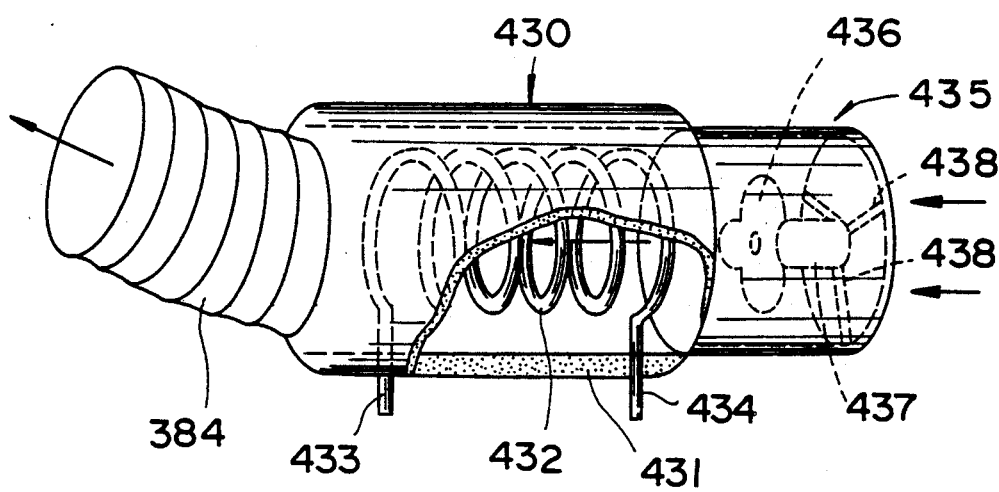

| ① 3 4 5 9 9 6 3 | 8 6 9 2 5 4 6 |
| 5 6 3 9 4 6 8 | 6 4 9 9 7 3 6 |
| ② 8 4 6 6 9 7 3 | 7 9 8 7 3 5 6 |
| 6 3 9 4 8 3 7 | 3 9 5 5 6 5 3 |
| ③ 3 9 7 4 8 2 5 | 9 5 5 3 8 4 6 |
| 8 5 2 5 3 4 7 | 6 8 3 9 9 6 5 |
| ④ 5 9 3 5 2 8 6 | 6 4 3 7 4 9 2 |
| 2 5 4 7 8 5 6 | 2 9 5 6 8 9 5 |

APPARATUS FOR INCREASING THE ACTIVITY OF THE HUMAN BRAIN

This is a continuation of Ser. No. 188,200, filed Apr. 28, 1988, now abandoned which is a continuation application of application Ser. No. 608,918, filed May 10, 1984 (now abandoned), which is a continuation of application Ser. No. 317,205, filed Nov. 2, 1981 (now abandoned).

BACKGROUND OF THE INVENTION

This invention relates to an apparatus for increasing the activity of the human brain.

It is an object of this invention to provide an apparatus for increasing the activity of the human brain which comprises means for cooling the head of a person and means for warming his feet or legs.

Another object is to provide an apparatus for increasing the activity of the human brain which comprises means mounted on the top of the back of a chair for cooling the head of a person and means disposed on the lower portion of the chair for warming his feet or legs.

Still another object is to provide an apparatus for increasing the activity of the human brain which comprises means for cooling the head of a person lying on a bed or mattress and means for warming his feet and legs.

A further object is to provide an apparatus for increasing the activity of the human brain which comprises means for cooling the head of a person sitting at a desk and means for warming his feet or legs.

A further object is to provide an apparatus for measuring the brain power of a person which is increased in brain activity by the use of such an apparatus for increasing the activity of the human brain as described hereinbefore.

According to one aspect of this invention, an apparatus for increasing the activity of the human brain comprises a cooling and warming device including a compressor for compressing a coolant such as Freon, a warming section in the form of a condenser for receiving the compressed coolant from the compressor and radiating heat, and a cooling section in the form of an evaporator for receiving the coolant from the condenser through a capillary tube and evaporating it for cooling. The compressor may be mounted in a chair. The evaporator may be mounted on the top of the back of the chair while the condenser may be mounted on the lower section of the chair. The condenser may include heat radiating pipes which are assembled into a foot rest mounted on the lower section of the chair. The evaporator may be mounted within a head rest on the top of the back of the chair. Further, the evaporator may be assembled into a pillow and connected with a box located aside of a bed or mattress through any suitable means such as hose, pipe and the like, the box housing the compressor therein. The box also receives the condenser from which the heated air is fed to a nozzle located adjacent to the feet of a person lying on the bed or mattress by means of a fan through any suitable means such as a hose, pipe and the like. Furthermore, the evaporator may be assembled into the lower section of the chair rather than the top of the back thereof. In this case, the cooled air is conducted from the evaporator near the head of the person through any suitable means such as a hose, pipe and the like.

In another aspect of this invention, the cooling means on the top of the back of the chair may comprise a head rest including a housing which has openings formed therein for causing air to pass into and out of the housing and, an electrically driven fan mounted within the housing for blowing air to the back of the head of a person through the outlet openings in the housing. In this case, the lower section of the chair includes a foot rest mounted thereon into which an electric heater is assembled. Furthermore, air may be blown toward the back of the head through any suitable moistened material such as cloth, felt, fibers and the like. In this case, the air can be cooled by means of liquid such as water as it passes through the moistened material.

In still another aspect of this invention, the apparatus comprises an electronic device utilizing the Peltier effect, which includes a thermoelement having a cold section positioned against the head of a person and a hot section located against his feet or legs.

In a further aspect of this invention, the apparatus may include a body adapted to be placed between the legs of a desk, the body housing a compressor, an evaporator and a condenser. Air is cooled at the evaporator and conducted toward the head of a person sitting at the desk through a flexible hose. He can rest his feet on the portion of the body which is heated by the condenser located therein.

This invention further provides an apparatus for measuring the brain power of a person which is increased in brain activity by means of the above-mentioned apparatus. The measuring apparatus comprises means receiving one finger of a person, means for radiating a light beam toward the finger, means for receiving the light beam transmitted through the finger to generate signals at the output thereof, and means for indicating the magnitude of the signals from the signal generating means. If a vertical or inclined column of liquid is heated near the bottom, the heated liquid will tend to rise in the column. If the outer arteries in the head are cooled, such cooled outer arteries will constrict, but if the same amount of blood is being pumped to the head, there will be a greater flow of blood in the inner arteries leading more directly to the brain because of the constriction in such outer arteries. Therefore, the combination of the heating of the feet and cooling of the outside of the head results in greater flow of blood to the brain, thereby increasing the activity of the brain.

These and other object, features and advantages of this invention will be apparent from reading the following detailed description of preferred embodiments with reference to the accompanying drawings:

BRIEF DESCRIPTION OF THE DRAWINGS

FIG. 13 is a front elevational view of another form of a chair which can be used in this invention;

FIG. 14 is a side elevational view of the chair in FIG. 13;

FIG. 15 is a top view of the chair in FIG. 13;

FIG. 16 is a bottom view of the chair in FIG. 13;

FIG. 19 is a schematic side view of another modification of the chair into which the apparatus of this invention is assembled;

FIG. 20 is a top view of a modification of the head rest of the chair into which the cooling section of the apparatus according to this invention is assembled;

FIG. 21 is a schematic side view, partially broken away, of still another modification of the chair into which the apparatus of this invention is assembled;

FIG. 22 is a fragmentary, schematic side view of a foot rest which can be used in the chair according to this invention;

FIG. 27 is a side elevational view, partially broken away, of a chair which is another embodiment of this invention;

FIG. 28 is a fragmentary section of a modification of the chair shown in FIG. 27;

FIG. 29 is a side elevational view of another modification of the chair according to this invention;

FIG. 30 is a view similar to FIG. 29, showing a further embodiment of this invention;

FIG. 31 is a schematic side view of a seat in an automobile to which this invention is applied;

FIG. 42 is an exploded, perspective view of another embodiment of the head rest according to this invention;

FIG. 43 is a side elevational view of the head rest shown in FIG. 42;

FIG. 44 is a side elevational view illustrating the relationship between the head of a person and the head rest shown in FIGS. 42 and 43 which is assembled into a chair;

FIG. 45 is a side elevational view of a pillow to which the embodiment shown in FIGS. 42 to 44 is applied;

FIG. 46 is a top view, partially broken away, of a head rest similar to the embodiment shown in FIGS. 42 to 45 but different from it in the cooling mechanism;

FIG. 67 is a fragmentary perspective view of one form of the nozzle which can be used in the embodiment of FIG. 61;

FIG. 68 is a view similar to FIG. 67, showing another form of the nozzle;

FIG. 69 is a perspective biew, partially broken away, of a cooling mechanism which can be used in the embodiment of FIGS. 59 to 66;

DESCRIPTION OF THE PREFERRED EMBODIMENTS

Figure 1:
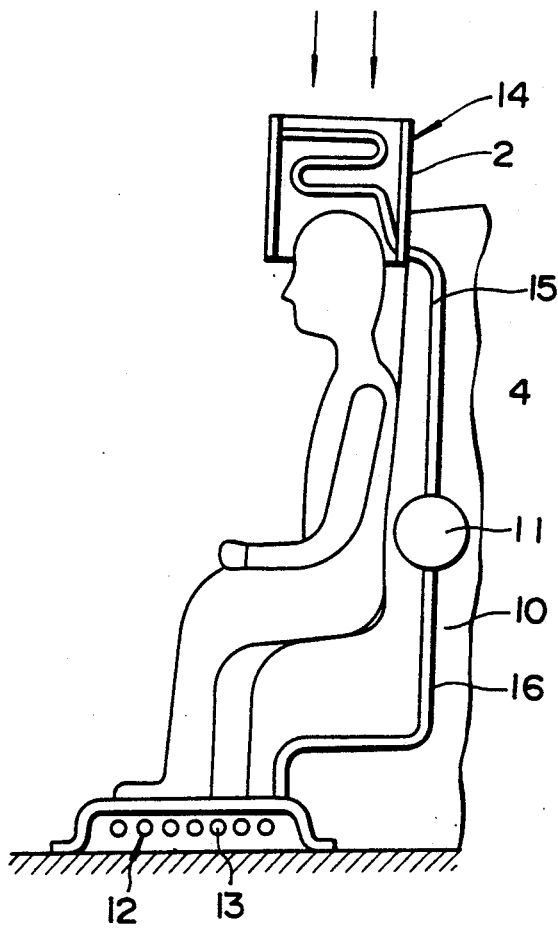
FIG. 1 is a schematic view illustrating the principle of this invention.
Figure 2:
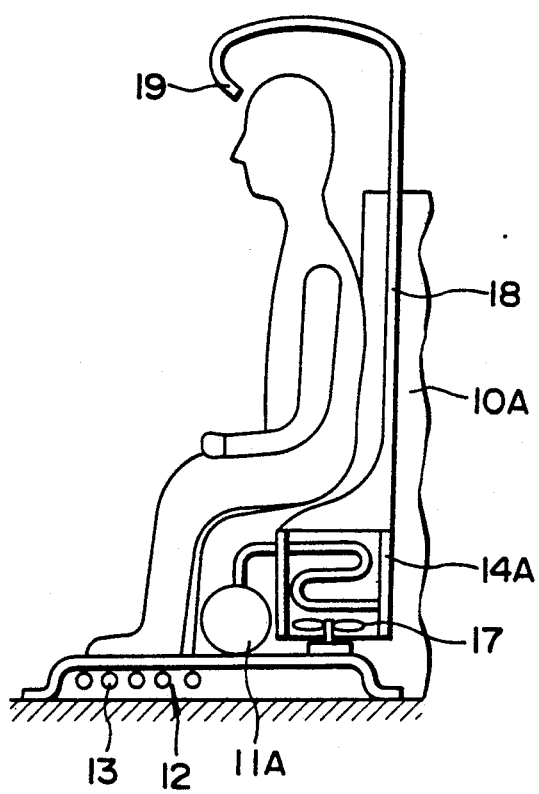
FIG. 2 is a schematic view of a modification of the form shown in FIG. 1.

Referring to FIG. 1, an apparatus for increasing the activity of the human brain comprises a chain 10, a compressor 11 housed in the back of the chair 10, a condenser section 12 in the form of a zigzagged pipe portion 13 which is mounted in a foot rest extending outwardly from the lower portion of the chair 10 and an evaporator section 14 mounted on the top of the back of the chair 10. The evaporator section 14 includes a cylindrical open-ended sleeve within which at least a portion of the head of a person sitting on the chair 10 can be placed, and which is formed from a cooling hollow plate member connected to the compressor through a pipe 15 for functioning as cooling means. The zigzaged pipe portion 13 in the condenser section 12 is also connected with the compressor 11 through a pipe 16 for functioning as warming means. When a person sits on the chair 10, his head is inserted into the cylindrical sleeve of the evaporator section 14 while his feet are placed on the foot rest which are being warmed by the condenser section 13. Thus, the person will be increased in brain activity by sitting on the chair 10 with the head cooled by the evaporator 14 and with the feet warmed by the condenser 12. The sitting period may vary and desired results have been achieved for a sitting period of 10 minutes. FIG. 2 shows a slightly different form of the chair according to this invention in which a compressor 11A is housed below the seat portion of the chair 10A. Adjacent to the compressor 11A is located a cylindrical evaporator sleeve 14A including a fan 17 which is disposed at the lower open end thereof. The upper open end of the sleeve 14A is connected with a pipe 18 which extends therefrom near the forehead of a person sitting on the chair 10A with the outlet 19 being positioned to blow air cooled at the evaporator sleeve 14A toward the forehead of the person. The condenser section 12 is mounted within the foot rest of the chair in the same manner.

Figure 4:
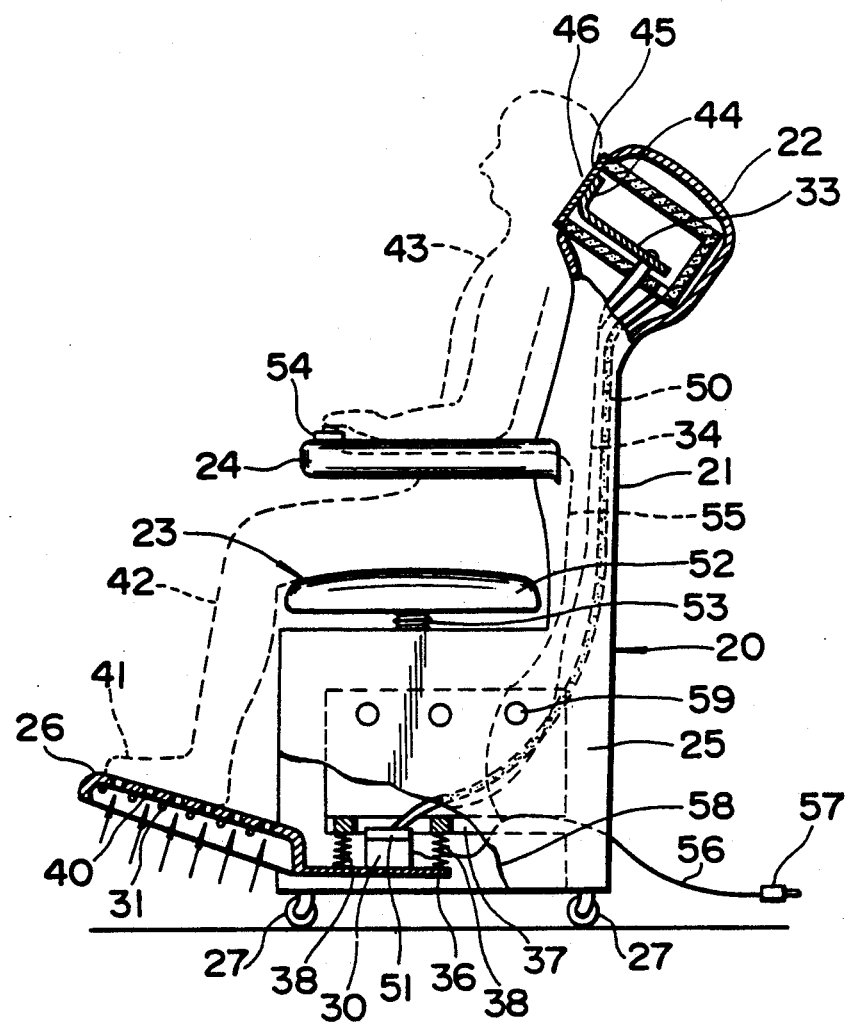
FIG. 4 is a side elevational view, partially broken and in section, of a chair into which one embodiment of this invention is assembled.
Figure 5:
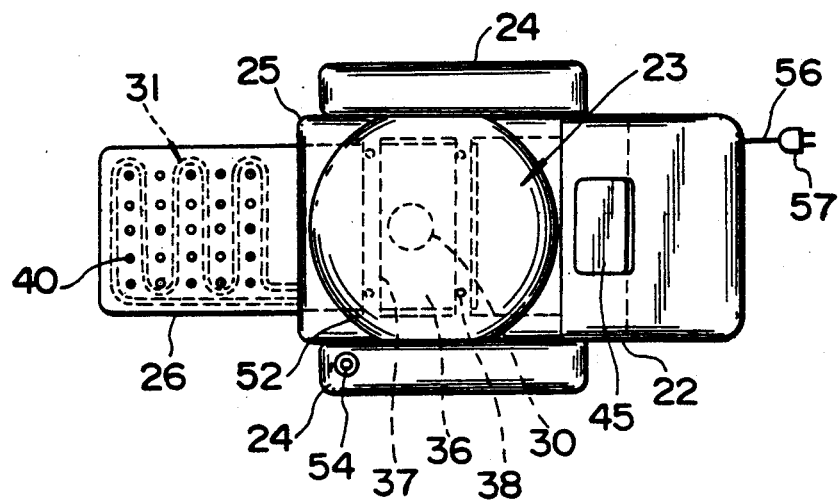
FIG. 5 is a top view of the chair shown in FIG. 4.

FIGS. 4 and 5 show a chair 20 of still another embodiment of this invention which comprises a back 21, a head rest portion 22 formed at the top of the back 21, a seat portion 23, armrests 24 extending from the back 21 above the seat portion 23, a lower box-like supporting portion 25 and a foot rest portion 26 extending outwardly and upwardly from the lower portion 25. The lower supporting portion 25 is provided with casters 27 which are mounted on the bottom thereof for moving the chair 20.

Figure 3:
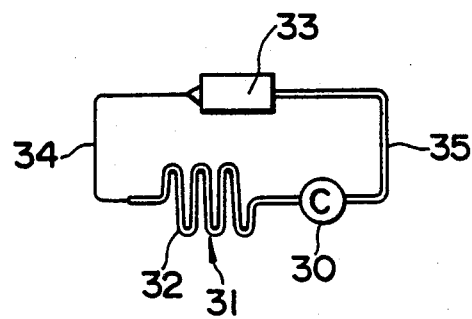
FIG. 3 is a circuit diagram showing the coolant circulation used in this invention.

A cooling-warming device as shown in FIG. 3 is assembled into the chair 20 and comprises a compressor 30 driven by an electric motor (not shown), a condenser section 31 in the form of a zigzaged heat-radiation pipe 32 which is connected with the compressor 30 downstream thereof, an evaporator section 33 connected with the outlet side of the condenser 31 through a capillary pipe 34 and a pipe portion 35 connecting the outlet side of the evaporator 33 with the compressor 30 at the inlet side thereof. The principle in such a cooling-warming circuit is well known in the art as in air conditioners. Therefore, it is understood that further description thereof is unncessary. It is also understood that such a circuit may use any suitable coolant such as Freon.

The compressor 30 is mounted on a plate member 36 which is suspended from the cross member 37 by means of springs 38 and which has a forward extension defining the perforated foot rest 26. The condenser 31 is mounted on the bottom face of the foot rest 26. Air is heated by the condenser 31 and then moved upwardly through the perforations 40 in the foot rest 25 to warm the feet 41 and legs 42 of a person 43 which sits on the chair 20 and is shown by a broken line in FIG. 4.

The condenser 31 is also connected, through the capillary pipe 34, with the evaporator section 33 which is mounted in a thermally insulating box 44 mounted in turn in the head rest portion 22 of the chair 20. The box 44 is opened in a direction opposed the back of the person's head with the opened end being closed by a cover sheet 45 of any heat-conductive and flexible sheet material such as metal sheet, plastic sheet or the like. In the illustrated embodiment, the evaporator 33 is in the form of a cooling plate having a L-shaped section with the smaller leg of the letter L being located opposed to the rearward or inward face of the cover sheet 45 and spaced away therefrom by only a slight distance. When the person's head 46 bears against the cover sheet 45, the latter is deformed inwardly into contact with the smaller leg of the cooling plate. Thus, the person's head 46 can be cooled by the evaporator 33 through the cover sheet 45. In such a manner, the evaporator 33 is thermally insulated relative to atmosphere so that the compressor 30 will not be overloaded.

The box 44 is provided with a drain pipe 50 for removing any waste water in the box 44 and conducting it to an evaporating dish 51 which is mounted on the top of the compressor 30.

The seat portion 23 includes a circular seat 52 which is screwed into a threaded hole (not shown) in the lower supporting portion 25 of the chair 20 through a threaded shaft 53 connected with the bottom of the circular seat 52 for adjusting the seat in height. Also, the rotatable seat 52 can be conveniently used by the person 43.

One of the armrests 24 is provided with a power switch 54 for controlling the motor (not shown) for the compressor 30. The power switch 54 is connected with the compressor motor through a line 55. The motor is adapted to be connected with a power supply (not shown) through a line 56 having a plug 57.

As can seen from FIG. 1, the lower supporting portion 25 of the chair 20 is provided with sidewalls 58 (only one shown) for covering the compressor section 30. The sidewalls 58 is formed with vents 59.

Figure 6:
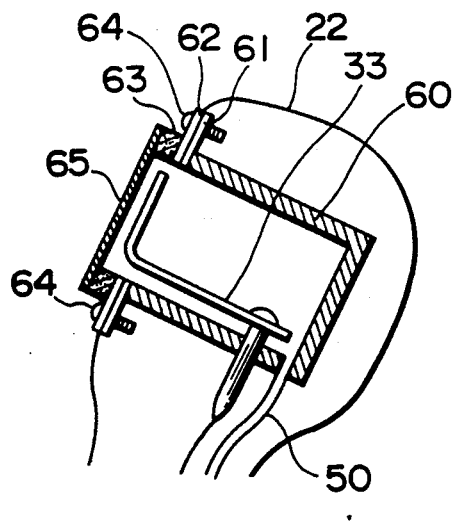
FIGS. 6 through 12 are schematic views, in section, of various forms of the head rest on the chair as shown in FIGS. 4 and 5, each of the head rests including a cooling section.

FIGS. 6–12 show various types of the cooling section in the cooling-warming circuit which is assembled into the head rest 22 of the chair 20 shown in FIGS. 4 and 5. In FIG. 6, the cooling section includes a thermally insulating box 60 having a flange 61 attached thereto at the forward opened end. On the flange 61 is mounted a flange 62 of a frame 63 through any suitable means such as screws 64, which frame 63 is made of an elastomeric material such as foamed urethane. The flange 62 can be bonded to the frame 63 by use of any suitable adhesive means. The frame 63 has a head-engaging plate 65 made of a metal or plastic sheet which is attached to the frame at the opposite side thereof by any suitable and spaced away from the cooling plate 33 by a slight distance means such as adhesive. When the person bears against the head-engaging plate 65 at his head, the plate 65 is urged inwardly into contact with the cooling plate 33.

Figure 7:
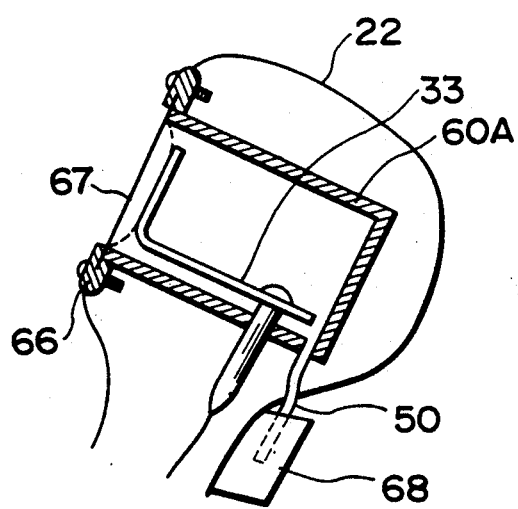

In FIG. 7, a thermally insulating box 60A includes clamping means 66 mounted thereon at its forward opened end. A flexible plastic film 67 such as PVC film is mounted on the box 60A by the clamping means 66 to close the forward opened end of the box 60A. The film 67 is spaced away from the cooling plate 33 by only a slight distance. Similarly, the film 67 can be urged inwardly into contact with the cooling plate 33 as shown by a dotted line in FIG. 7. In this embodiment, the drain pipe 50 is connected to a vessel 68 which is detachably mounted on the lower end of the head rest 22.

Figure 8:
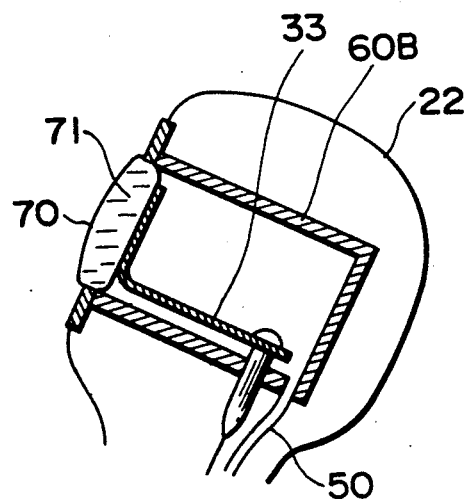

In FIG. 8, a thermally insulating box 60B includes a flexible vessel 70 as made of plastic sheet materials which is mounted thereon at its forward opened end through any suitable means. The flexible vessel 70 contains a liquid 71 having low freezing temperature such as 50% aqueous solution of ethylene glycol, propylene glycol, agar solution or the like. The flexible vessel 70 is continuously engaged by the cooling plate 33.

Figure 9:
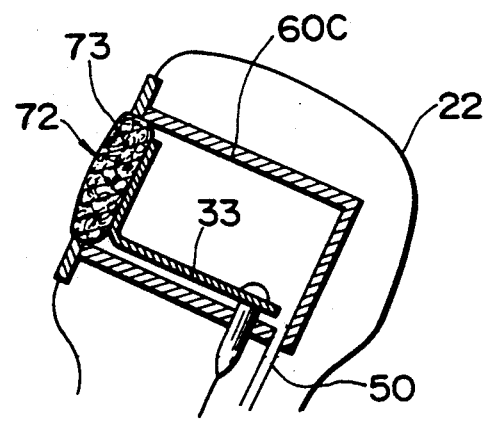

A thermally insulating box 60C shown in FIG. 9 includes a cushion and heat-conductor 72 mounted thereon at its forward opened end by any suitable manner. The cushion and heat-conductor 72 includes a mass of aluminum wires or steel wool 73 and a cover 74 enclosing the mass 73.

Figure 10:
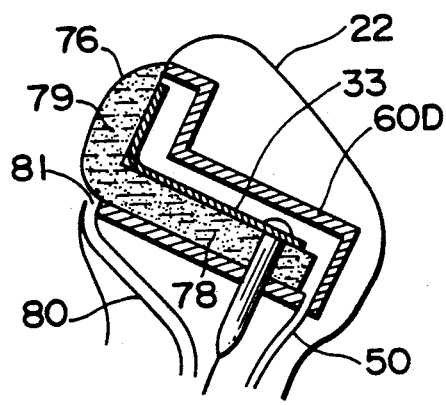

FIG. 10 shows a thermally inculating box 60D which has its L-shaped section different from the previous embodiments but similar to the shape of the cooling plate 33. This embodiment includes a ceramic member 76 having substantially a L-shaped section which extends along the L-shape of the cooling plate 33. The ceramic member 76 includes a longer leg portion 78 extending into the box 60D along the corresponding leg portion of the cooling plate 33 and a shorter leg portion engaged by the corresponding shorter leg of the cooling plate 33 and serving as a closure for the forward opened end of the box 60D. In addition to the drain pipe 50, there is another drain pipe 80 with the inlet 81 thereof for receiving droplets of water which will be condensed at the outward face of the ceramic member 76.

Figure 11:
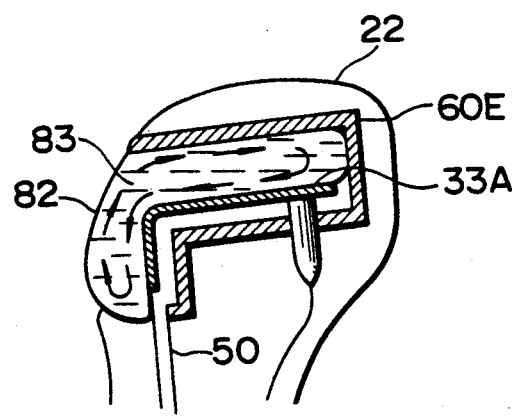

In FIG. 11, a thermally insulating box 60E has an inverted L-shape section and is inclined forwardly and downwardly for a reason which will be appraent hereinafter. The box 60E includes a cooling plate 33A disposed at the same state in shape and position as that of the box 60E and spaced away from the inner wall of the box 60E. A plastic bag 82 is disposed to extend along the entire upper surface of the cooling plate 33A and into the box 60E. Thus, the plastic bag 82 having substantially its inverted L-shape section is formed with the leg portion closing the forward opened end of the box 60E. The bag 82 contains an anti-freeze liquid 83. When the bag 82 is engaged by the head of the person, the anti-freeze liquid 83 is circulated in the bag 82 as shown arrows in FIG. 11 to cool the person's head more effectively. The circulation of the liquid 83 is promoted by the inclination of the box 60E. In this case, the condensed water is accumulated at the bottom of the shorter leg portion of the box 60E. Therefore, the drain pipe 50 is also attached to the bottom of the shorter leg of the box 60E.

Figure 12:
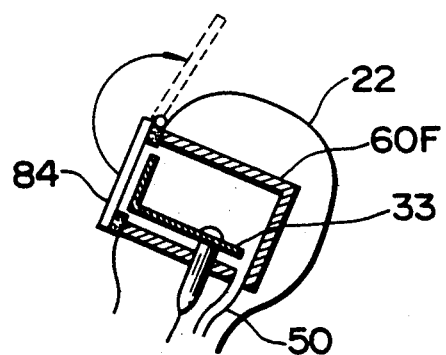
Figure 17:
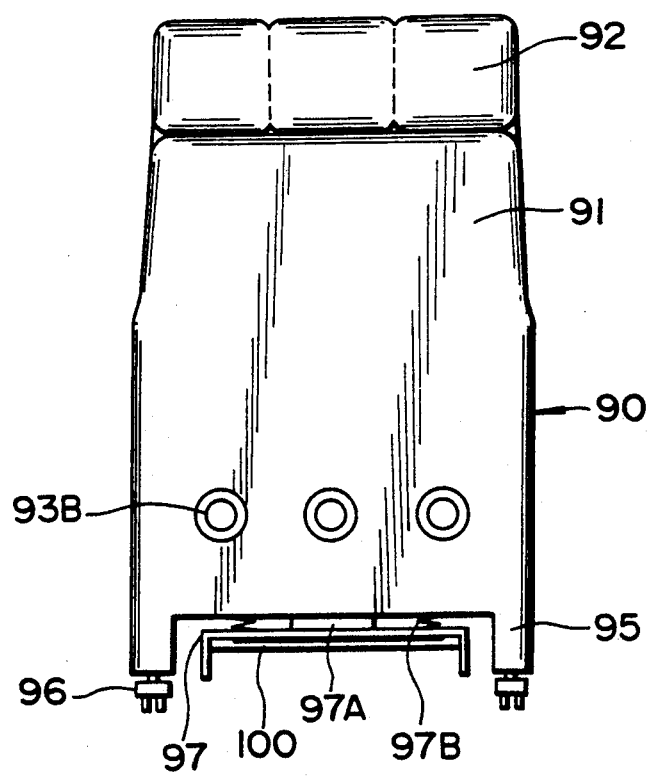
FIG. 17 is a rear view of the chair in FIG. 13.

In an embodiment shown in FIG. 12, a thermally insulating box 60F includes a rigid lid 84 closing the forward opened end thereof. The lid 84 is hinged at its upper edge to the box 60F. In use, the lid 84 is opened to a position shown by a broken line in FIG. 12 so that the person's head will be contacted directly with the cooling plate 33.

FIGS. 13 to 17 show another example of the chair into which the cooling and warming circuit according to this invention is assembled. This embodiment includes a chair 90 having a back 91, a head rest 92 formed at the top of the back 91, a base 93 supporting the back 91 and having a seat 93A and armrests 94, legs 95 supporting the base 93 and having casters 96 mounted thereon at the lower end thereof, and a foot rest 97 extending outwardly from between the forward legs 95 of the base 93 and suspended from the cross beams 93C of the base 93 by means of springs 97B. A cooling and warming circuit used in this chair comprises a compressor 97A mounted on the foot rest 97 below the bottom of the base 93, an evaporator as cooling section connected to the compressor 97A and including a portion exposed at the head rest 92 as shown by 92A, and a zigzaged condenser pipe 100 as warming section disposed on the bottom of the foot rest 97. This foot rest 97 has a plurality of small openings 98 for permitting the upward movement of warmed air at the condenser pipe 100. The base 93 has vents 93B formed therein at the side walls for causing air heated at the compressor 97A to escape to atmosphere.

Figure 18:
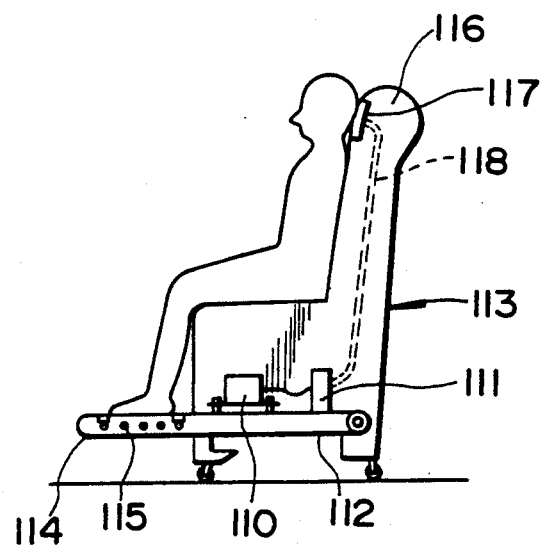
FIG. 18 is a schematic side view of a modification of the chair into which the apparatus of this invention is assembled.

FIG. 18 shows another embodiment of this invention in which a cooling and warming circuit includes a compressor 110 and an evaporator 111 mounted on a base plate 112 which is pivotally mounted on a chair 113 at the rearward end thereof and suspended from the bottom of the chair 113 at the intermediate part of the base plate 112 by means of springs (not shown). The forward portion of the base plate 112 extends forwardly and outwardly from the bottom of the chair 113 to form a foot rest 114 into which a condenser 115 of the cooling and warming circuit is assembled.

The chair 113 has a head rest on which a cooling terminal 117 having any suitable shape and being made of any heat-conductive material such as copper, aluminum or the like is mounted. The cooling terminal 117 is connected with the evaporator 111 through a heat pipe 118 which passes through the back of the chair 113 and which, as well known, comprises a pipe containing fibers and a liquid therein. Such a heat pipe is well known in the art and is not further explained herein.

In another embodiment shown in FIG. 19, a cooling and warming circuit comprises a compressor 120 and an evaporator 121 all of which are mounted within the bottom of a chair 122. This circuit also includes a condenser 123 mounted within a foot rest 124 of the chair 122.

The chair 122 has a head rest 125 having a plurality of openings 126 formed therein at the forward wall thereof. These openings 126 are connected to fan means 127 through a pipe 128. The fan means 127 is mounted on the evaporator 121 to supply air cooled thereat to the head rest 125 through the pipe 128. Thus, cooled air is blown from the head rest 125 toward the person's head through the openings 126.

FIG. 20 shows a modified embodiment of this invention in which a head rest 130 includes apertures 131 formed therein at the sides thereof for blowing the cooled air toward the sideward and rearward portions of the person's head 132.

FIG. 21 shows another modified embodiment of this invention in which a chair 140 includes a seat portion 141 with a back 142, and a base portion 143 having a foot rest 144 and containing a compressor 145 and an evaporator 146 therein. A condenser 147 is assembled into the foot rest 144 as in the previously mentioned embodiments. Air is cooled at the evaporator 146 and conducted to the forehead of a person through a duct 148 by means of a fan (not shown) which is mounted in the evaporator unit.

FIG. 22 shows a modified embodiment of the foot rest according to this invention. In this embodiment, a foot rest 150 includes a forward portion 151 and a rearward portion 152. The forward portion 151 of the foot rest 150 has a top plate 153 curved upwardly at that portion of the foot rest 150 corresponding to the arches of the person's feet 154. The rearward portion 152 of the foot rest 150 is suspended from transverse studs 155 on the legs 156 of a chair (not shown) by means of springs 157, and supports a compressor 158 of the cooling and warming circuit. Thus, any vibration of the compressor 158 is not transmitted to the chair. However, the vibration from the compressor 158 serves to massage the person's feet 154 on the forward portion 151 of the foot rest 150. The forward portion 151 includes an condenser 159 of the cooling and warming circuit mounted on the bottom of the top plate 153 in the same manner as those of the previously mentioned embodiments. Further, this embodiment includes a power switch 158A for the cooling and warming circuit which can be actuated by the thumb of the person's foot 154.

Figures 23, 24:
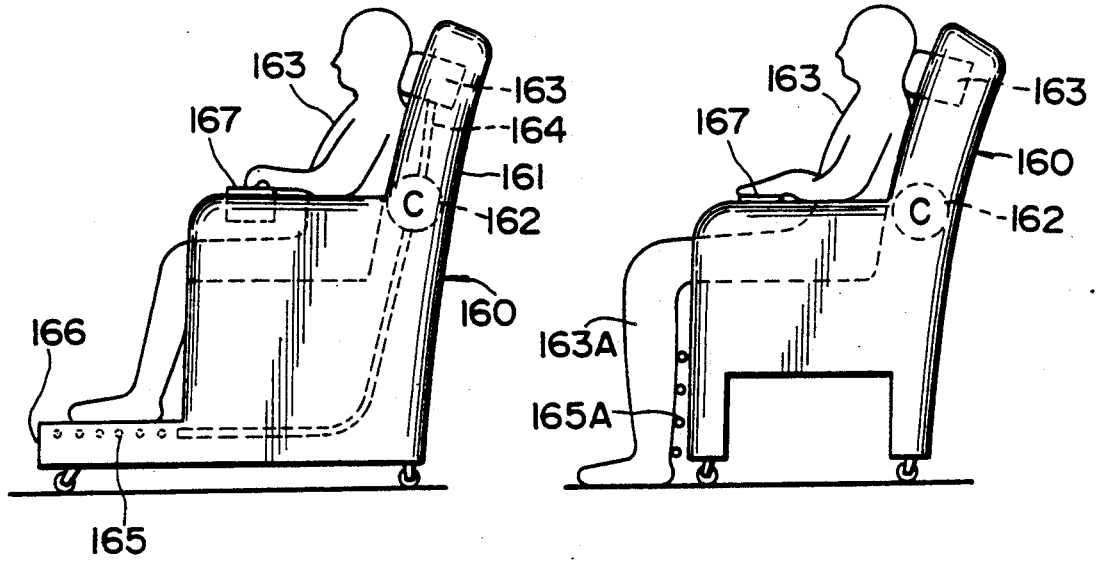
FIGS. 23 through 26 are side elevational views of various embodiments of this invention which are embodied in the form of a chair.

FIG. 23 shows another embodiment of this invention in which a chair 160 has a back 161 including a compressor 162 mounted therein for serving to massage the bach of a person 163. The compressor 162 is connected to an evaporator section 163 on the top of the back 161 of the chair 160 through a pipe 164, and coupled with a condenser 165 which is mounted in a foot rest 166 formed integrally of the chair 160 and extending forwardly therefrom. The chair 160 also includes a power switch 167 for controlling the actuation of the compressor 162.

A chair 160 shown in FIG. 24 has substantially the same construction as that of the chair shown in FIG. 23 except that a condenser 165A is located forwardly of the forward face of the chair 160, that is, rearwardly of the legs 163A of the person 163 sitting on the chair 160 without any foot rest.

Figures 25, 26:
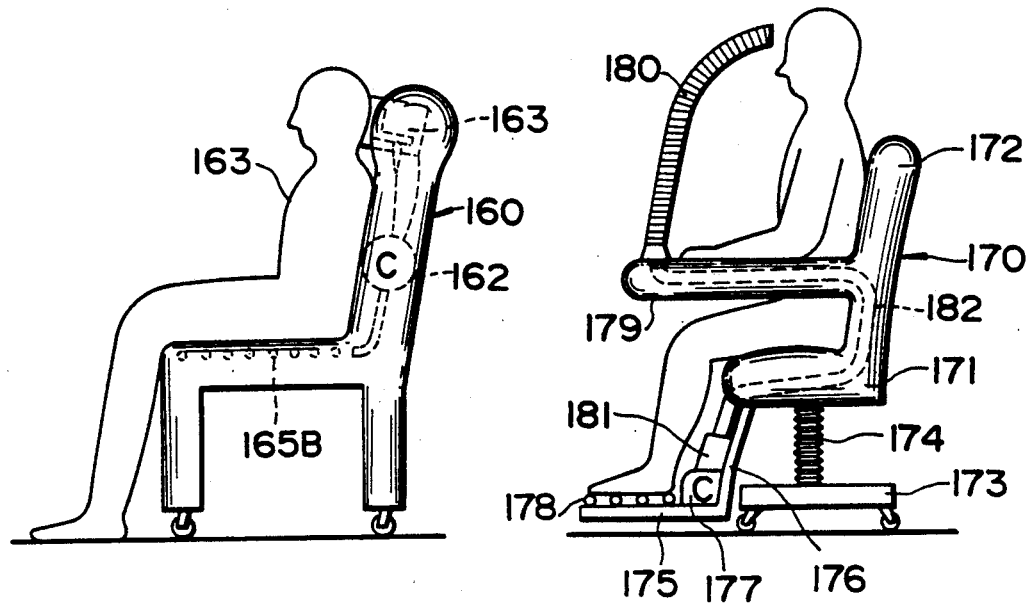

FIG. 25 shows a chair 160 having substantially the same construction as that of the chair shown in FIG. 23 except that a condenser 165B is disposed below the seat portion of the chair 160 for warming the buttocks and thighs of the person 163 which sits on the chair 160.

FIG. 26 shows another embodiment of the chair of this invention in which a chair 170 includes a seat portion 171 with a back 172, the seat portion being screwed to a base portion 173 through a threaded shaft 174. The seat portion 171 also includes a foot-rest portion 175 suspended therefrom through a substantially vertically extending plate 176. Adjacent to this plate 176 is mounted a compressor and evaporator unit 177 on the foot-rest portion 175. A condenser 178 is mounted on the foot-rest portion 175 forwardly of the unit 177.

Armrests 179 extends forwardly from the back 172 of the seat portion 171. One of the armrest 179 has an upwardly extending duct 180 mounted thereon at the forward end. The duct 180 has one opened end located near the forehead of a person sitting on the chair 170 with the other opened end being connected with the compressore and evaporator unit 177 through fan means 181 via a pipe 182 which passes through the seat portion 171, the lower part of the back 172 and the one armrest 179. Air is cooled at the compressor and evaporator unit 177 and conducted therefrom to the forehead of the person through the pipe 182 and duct 180.

FIG. 27 shows one embodiment of this invention in which the cooling and warming device including the compressor, evaporator and condenser is not used therein. In this embodiment, a chair 190 comprises a base portion 191 having a foot rest 192, a seat portion 193 connected with the base 191 through a thread and screw mechanism 191A, a back 194 connected integrally with the seat 193, and a head-rest portion 195 formed on the top of the back 194. The head-rest portion 195 includes a fan 196 driven by an electric motor 196 all of which are mounted within therein. A plurality of openings 198 are formed in the forward wall of the head rest 195 ahead of the fan 195 while a plurality of another openings 200 are formed in the rearward wall of the head rest 195 behind the motor 197. If the fan 196 is driven by the motor 197, air is drawn into the head rest 195 through the rearward openings 200 and then blown to the head of a person sitting on the chair 190 through the forward openings 198.

The electric motor 197 is connected to a power supply (not shown) through an electric line 201 having a plug 202. The electric line 120 is electrically connected to an electric heater 203 which is mounted in the foot rest 192. The forward wall of the head rest 195 also has a power switch 204 for controlling the electric motor 200 and heater 203. When the power switch 204 is actuated by the head of the person sitting on the chair, the electric motor 200 and heater 203 are energized to cool the head of the person with the blown air and to warm the feet of the person with the heat from the heater.

FIG. 28 shows an embodiment similar to that of FIG. 27 except that a sheet of roughly woven cloth 210 is located in the head rest 195A to block the flow of air from the fan 196. The cloth 210 is immersed at the upper end in the water contained in a vessel 211 which is mounted on the top of the head rest 195A. The vessel 211 has a central open-ended tube portion 212 which extends inwardly of the vessel 211 for conducting the one end of the cloth 210 to the water in the vessel. The other or lower end of the cloth 210 is received into another vessel 213 mounted on the inner wall of the head rest 195A at the lower end thereof. Air can be more cooled by passing through the wet cloth 210 under the action of evaporation heat.

FIG. 29 shows an embodiment of this invention which utilizes an electronic device based on the Peltier effect. This electronic device comprises a thermoelement 220 having a cold section 221 which is disposed on the head rest of a chair 222 against the head of a person sitting on the chair 222. The electronic device also includes a hot section 223 which is located in the head rest of the chair 222 and connected to a warming section in the foot rest 224 of the chair 222 through a heat pipe 225.

In an embodiment shown in FIG. 30, an electric motor 230 and a fan 231 are mounted in a separate head-rest 232 which is adapted to be detachably mounted on a chair 233 with the downwardly extending rod 234 thereof attached to the back of the chair 233. The feet of a person 235 sitting on the chair 233 can be warmed by an electric heater 236 placed on the floor 237.

FIG. 31 shows an embodiment of this invention which is applied to a seat 240 in an automobile 241. The seat 240 has a back 242 and a head rest 243 which includes a cooling means 244 mounted therein. The feet of a driver 245 can be warmed by the warmed air from the conventional heater (not shown) of the automobile 241, as shown by arrows.

Figure 33:
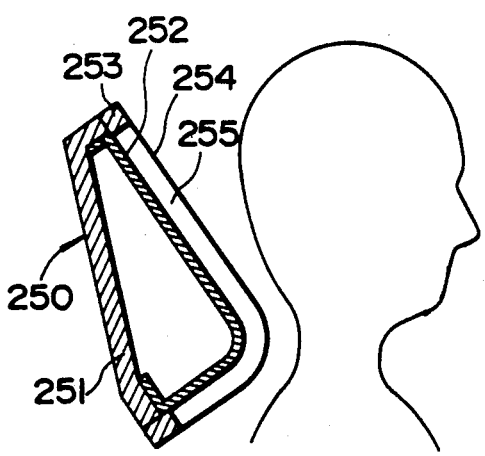
FIG. 33 is a side sectional view of the head rest shown in FIG. 32.
Figure 32:
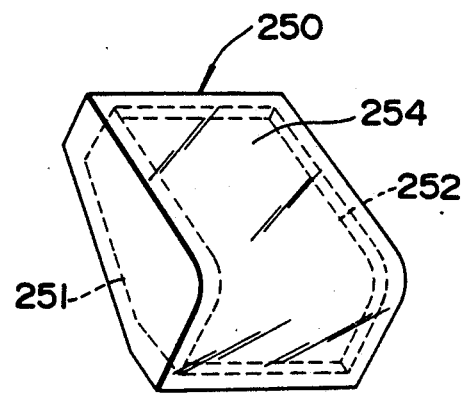
FIG. 32 is a perspective view of a head rest in a chair which is another embodiment of this invention.
Figure 34:
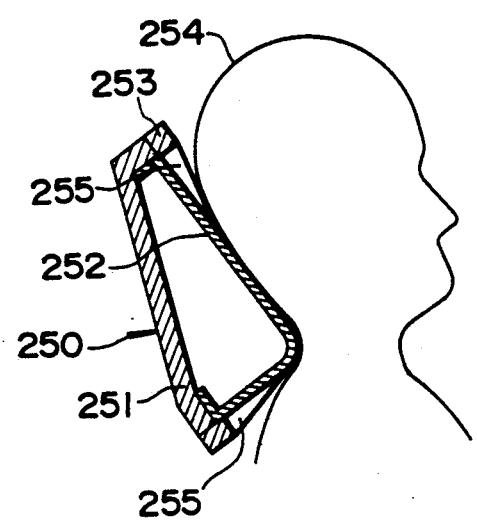
FIG. 34 is a view similar to FIG. 33, showing the head rest in such a state that the head of a person rests thereagainst.

FIGS. 32, 33 and 34 show another form of the head rest which includes a cooling section, for example, the evaporator section of the cooling and warming circuit utilizing a coolant such as Freon. In this embodiment, a head rest 250 comprises a casing 251 of any thermally insulating material such as foamed polyethylene or the like, and a cooling plate 252 mounted on the casing 251 by any suitable means. A frame 253 is mounted on the outer edge of the casing 251. On the outer face of the frame 253 is mounted a flexible sheet 254 to cover the cooling plate 252 entirely. Thus, an air layer 255 is formed between the cooling plate 252 and the flexible sheet 254 so that the former can be thermally insulated from atmosphere. However, when a person bears against the head rest 250 at his head, the flexible sheet 254 is deformed inwardly to bring the person's head into engagement with the cooling plate 252 through the flexible sheet 254. The flexible sheet 254 is made of any suitable elastomeric, heat-conductive and low-temperature resistance material such as a silicon rubber sheet containing metal powder therein, for example.

Figure 35:
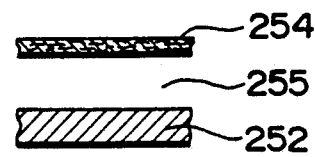
FIG. 35 is a fragmentary section illustrating the construction of the head rest shown in FIGS. 32 to 34.
Figure 36:
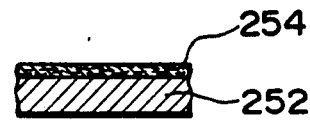
FIG. 36 is a view similar to FIG. 35, showing the construction of FIG. 35 in a different position.

FIGS. 35 and 36 illustrate such a state that the flexible sheet 254 is urged inwardly into engagement with the cooling plate 252 so that the air layer therebetween will be eliminated.

Figure 37:
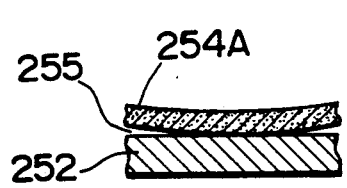
FIG. 37 is a fragmentary section illustrating another construction of the head rest shown in FIGS. 32 to 34.

FIG. 37 shows a silicon rubber sheet 254A containing aluminum powder therein which is deformed inwardly against the cooling plate 252.

Figure 38:
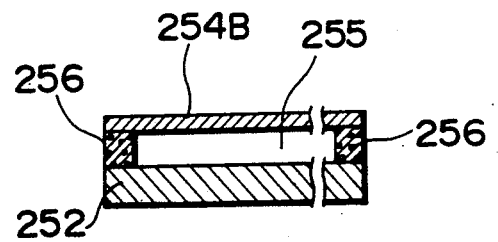
FIG. 38 is a view similar to FIG. 37, showing still another construction of the head rest shown in FIGS. 32 to 34.

FIG. 38 shows another form of the cover plate 254 in which a metal sheet such as aluminum sheet is used in place of the flexible sheet 254. In this form, the metal sheet 254B is mounted on the cooling plate 252 through cushion members 256 of any elastomeric material such as polyurethane foam. The sheet 254A can be moved inwardly parallel to the cooling plate 252. A polyester film can be used in place of the metal sheet 254A.

Figure 39:
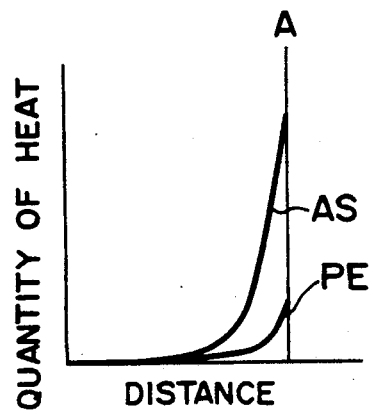
FIG. 39 is a graph showing the characteristics of cover materials used in the head rest of this invention.

FIG. 39 is a graph indicating the relationships between the quantity of heat transmitted from the cooling plate to the human head through the flexible sheet and the distance from the flexible sheet to the cooling plate, in various material sheets. A vertical axis indicates the quantity of heat while a horizontal axis represents the distance. In this graph, another vertical line A shows a position in which the sheet is in contact with the cooling plate. A curve PE shows the above relationship in a polyester sheet while another curve AS shows the relationship in a silicon rubber sheet containing aluminum powder therein. It is understood from this graph that the silicon rubber sheet is better in heat-conduction than the polyester sheet. However, this invention includes the use of any other similar material such as polyvinyl cloride, polyethylene or the like, in addition to the polyester sheet and the silicon rubber sheet.

Figure 40:
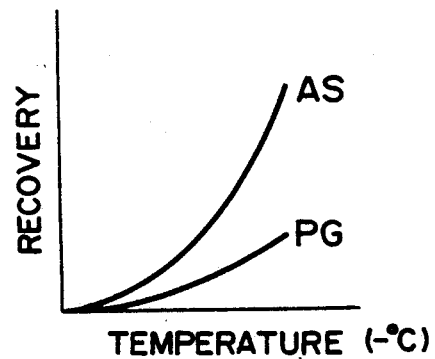
FIG. 40 is a graph showing the other characteristics of cover materials used in the head rest of this invention.

FIG. 40 shows a graph indicating the relationships between the recovery and the temperature, in various sheet material. A vertical axis indicates the recovery while a horizontal axis represents the temperature. A curve AS shows the above relationship in the silicon rubber sheet containing the aluminum powder while a curve PG shows the relationship in polyvinyl cloride or rubber. It is understood from this graph that the silicon rubber sheet is more suitable for this invention since it has maintained its recovery at lower temperature.

Figure 41:
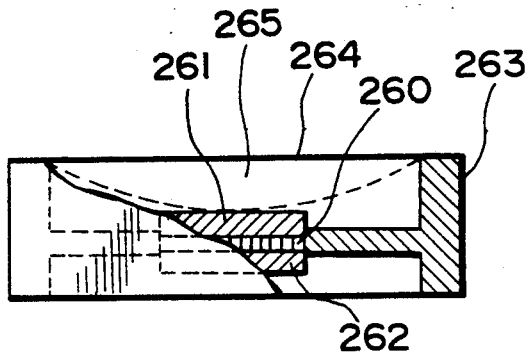
FIG. 41 is a top view, partially broken away, of another embodiment of the head rest according to this invention.

FIG. 41 shows an embodiment of this invention which is similar to the embodiment shown in FIGS. 32 to 34. This embodiment is, however, different from the previous embodiment in that an electronic device utilizing the Peltier effect is used as a cooling and warming system. The electronic device comprises a thermoelement 260 having a cold section 261 and a hot section 262. The thermoelement 260 is mounted in a heat-insulating frame 263 with the cold section 261 faced to a flexible sheet 264 which is mounted on the fram 263 across the opened end thereof. Between the flexible sheet 264 and the cold section 261 of the thermoelement 260 is formed an air gap 265.

FIGS. 42, 43 and 44 show a modification of the embodiment of FIGS. 32 to 34 in which a head rest 270 comprises an opened casing 271 of plastic sheet, a cooling element 272 housed within the casing 271 which element is, for example, in the form of such an evaporator as used in the previously mentioned embodiments, thermally insulating walls 273 as made of polyethylene foam covering the outer walls of the casing 271, and a closure member 274 closing the opening of the casing 271 and being adapted to be engaged by the head of a person.

The casing 271 includes a drain pipe 275 connected to a drain port 276 formed in the casing wall. The cooling element 272 housed in the casing 271 includes a capillary pipe 277 extending outwardly through the casing wall and the thermally insulating wall and connected with a compressor (not shown).

The closure member 274 has a substantially L-shaped form corresponding to the profile of the opening in the casing 271 and comprises a similarly L-shaped frame 278 having an opening 278A formed therethrough, an outer flexible sheet 279 attached to the outer face of the frame 278 by any suitable manner, and an inner flexible sheet 280 mounted on the inner face of the frame 278 by any suitable manner. There is an air space formed between the outer and inner sheets 279 and 280 within the opening 278A of the frame 278. The frame 278 is provided with a drain pipe 281 which is connected with an aperture 282 formed in the frame 278 for communicating with the air space between the outer and inner sheet 279 and 280. The closure member 274 is mounted on the casing 271 at the opening thereof by any suitable manner with the inner flexible sheet 280 spaced away from the surface of the cooling element 272 by only a slight distance therebetween.

The so formed head rest 270 can be mounted on the top of a back 284 in a chair (not shown) as seen from FIG. 44. When a person 285 bears against the closure member 274 of the head rest 270 exerting pressure thereon as shown by a broken line in FIG. 44, the outer and inner flexible sheets 279 and 280 are urged inwardly with the inner sheet engaged by the surface of the cooling element 272. Thus, the head of the person 285 will be placed in a thermal transmission with the cooling element 272. In unuse, the cooling element 272 can be thermally insulated from atmosphere by means of the air space in the frame 278 and the air layer between the inner sheet 280 and the surface of the cooling element 272 with no condensation of water on the outer surface of the closure member 274.

The outer and inner flexible sheets used in this embodiment can be made of a flexible sheet material having low-temperature resistance up to about −20° C. and heat-conduction, such as silicon rubber sheet containing aluminum powder, polyester film or metal sheet. Among them, the silicon rubber sheet is preferably used in this invention. Furthermore, A certain non-flexible sheet material can be used in this invention if it has the above characteristics. In such a case, the frame 278 is formed of a deformable cushion material such as urethane foam or the like.

FIG. 45 shows a pillow to which the concept of the embodiment shown in FIGS. 42 to 44 is applied. In this figure, similar parts are shown by similar numerals affixed by alphabet A or B.

FIG. 46 shows another example of the concept of FIGS. 42 to 45 in which an electronic device utilizing the Peltier effect is used as a cooling and warming device. The electronic device comprises a thermoelement 290 mounted on an open-ended frame 291 of thermally insulating material and having a cold section 292 and a hot section 293. A closure member 294 similar to the closure members 274 and 274A in the previously mentioned embodiments is mounted on the frame 291 at the opening thereof faced to the cold section 292 of the thermoelement 290. The closure member includes a frame 295, an outer flexible sheet 296 bonded to the outer face of the frame 295, and an inner flexible sheet 297 connected to the inner face of the frame. Similarly, when a pressure is exerted to the flexible sheets 296 and 297 as shown by an arrow 298 in FIG. 46, these sheets can be deformed inwardly with the inner sheet 297 engaged by the cold section 292 of the thermoelement 290.

Figure 47:
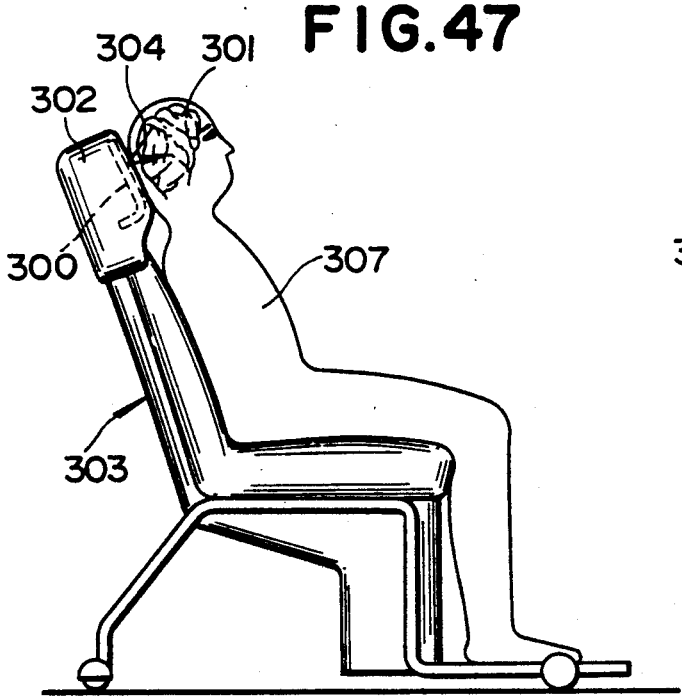
FIG. 47 is a schematic side view of a chair which is another embodiment of this invention.
Figure 51:
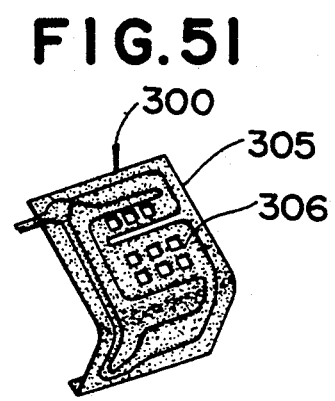
FIG. 51 is a perspective view of a cooling section used in the embodiments shown in FIGS. 47 to 50.

FIG. 47 shows other embodiment of this invention in which a cooling element 300 is made of a sheet material reflecting alpha wave from the human brain 301 back to the same as shown by an arrow 304, such as aluminum sheet. This sheet is assembled into a head rest 302 of a chair 303. The cooling element 300 comprises a plate 305 formed with a passage 306 for circulating a coolant such as Freon as shown in FIG. 51. The cooling element 300 serves to return alpha wave from the brain 301 of a person 307 sitting on the chair 303 back to the same for increasing the amount of the alpha wave therein.

Figure 48:
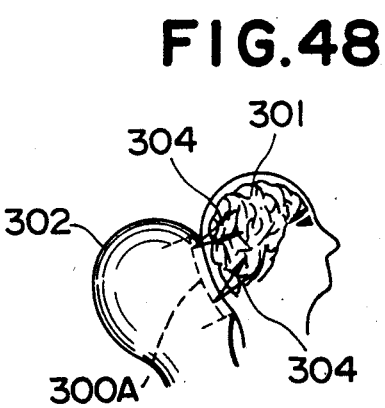
FIG. 48 is a fragmentary side view showing the head rest which is different from that of the embodiment shown in FIG. 47 in construction.

FIG. 48 shows a similar cooling element 300A except that it is made of a polyester film deposited with aluminum or a silicon rubber sheet containing aluminum powder.

Figure 49:
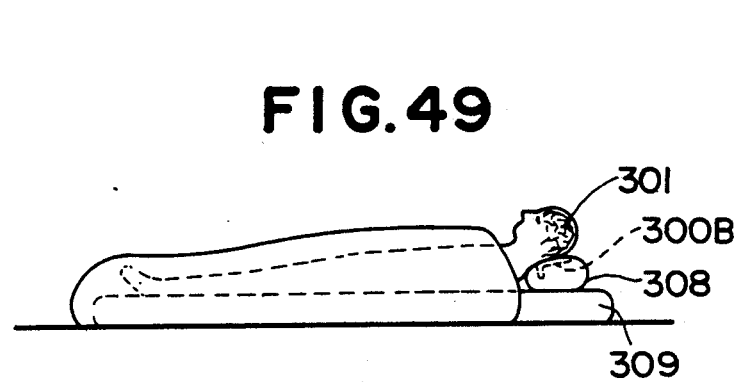
FIG. 49 is a side elevational view of a pillow to which the embodiment shown in FIGS. 47 and 48 is applied.

FIG. 49 shows an example in which an alpha-wave reflecting and cooling element 300B is assembled into a pillow 308 which is used on a bed or mattress 309.

Figure 50:
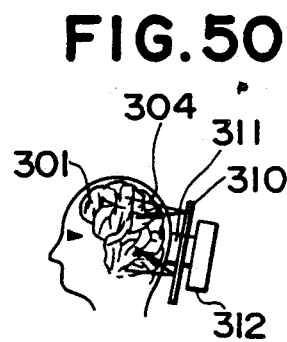
FIG. 50 is a side elevational view of a head rest which is a further embodiment of this invention.

FIG. 50 shows another example in which an alpha-wave reflecting and cooling plate 310 is mounted around the cold section 311 of a thermoelement 312.

Figure 52:
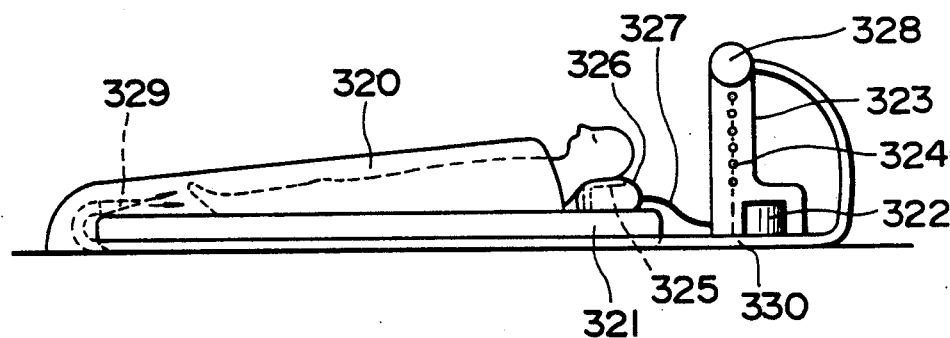
FIG. 52 is a side elevational view of still a further embodiment according to this invention in which the apparatus is utilized for a person lying on a mattress.
Figure 53:
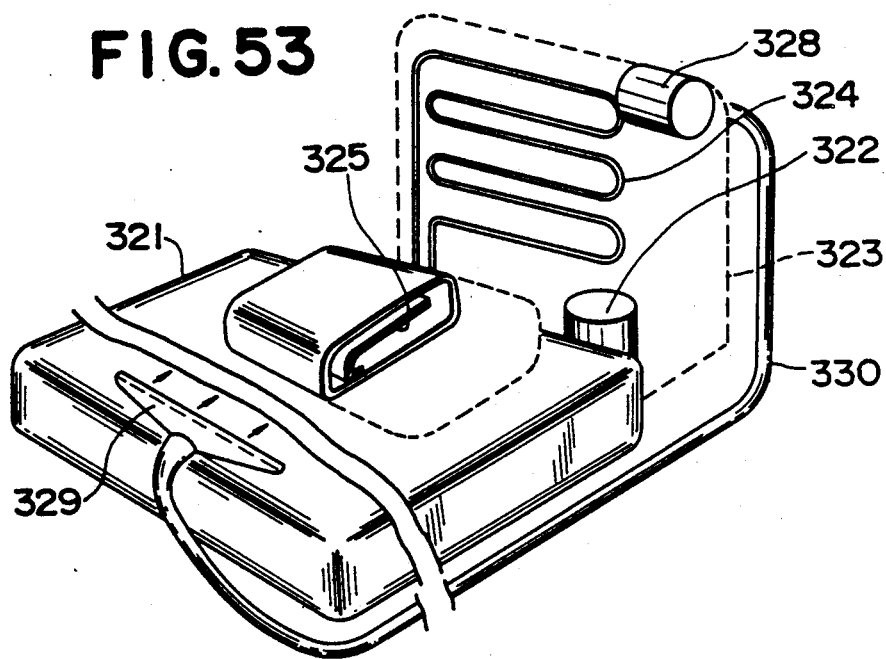
FIG. 53 is a perspective view, partially broken away, of the apparatus shown in FIG. 52.

Referring to FIGS. 52 and 53, the concept of this invention is applied for a person 320 lying on a mattress 321 or a bed. In this embodiment, a cooling and warming circuit comprises a compressor 322 received in a housing 323 and driven by any suitable means such as electric motor, a condenser 324 consisting of a zigzaged heat-radiation pipe which receives a compressed coolant such as Freon from the compressor 322 and similarly housed in the housing 323, and an evaporator 325 mounted in a pillow 326 and being in the form of a cooling element which receives the coolant from the condenser 324 through a capillary pipe 327 and evaporates the same. A blower 328 is mounted on the top of the housing 323 for feeding air heated by contacting with the condenser 324 to a nozzle 329 placed at the feet of the lying person 320 through a flexible hose 330. Thus, the person 320 lying on the mattress 321 will be cooled at his head and warmed at his feet.

Figure 54:
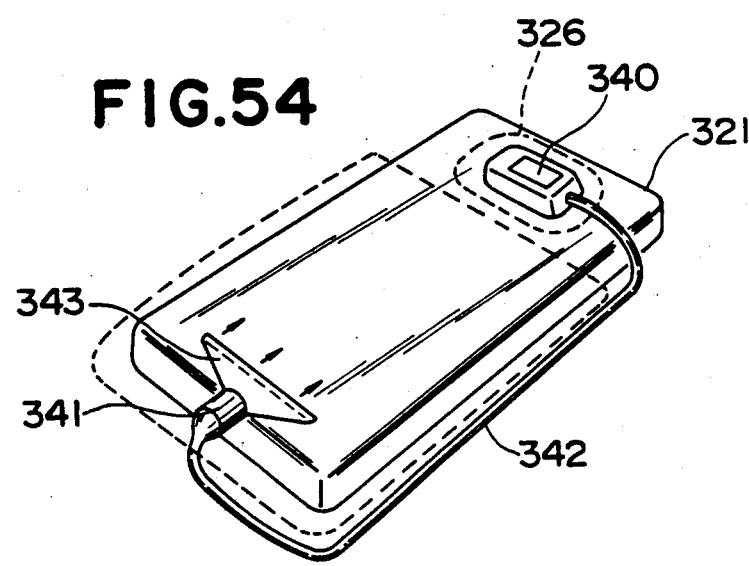
FIG. 54 is a perspective view of a modification of the embodiment shown in FIGS. 52 and 53.

FIG. 54 shows a modification of the embodiment shown in FIGS. 52 and 53 in which there is used a thermoelement 340 housed in a pillow 326 and including a cold section disposed against a pillow portion which is engaged by the head of a person (not shown) lying on a mattress 321, and a hot section located in the opposite side to the cold section in pillow 326. The hot section of the thermoelement 340 is connected to a blower 341 placed at that portion of the mattress 321 adjacent to the feet of the person lying on the mattress 321 through a flexible hose 342. A nozzle 343 is mounted on the outlet of the blower 341 for blowing air warmed by the hot section of the thermoelement 340 against the feet of the lying person.

Figure 55:
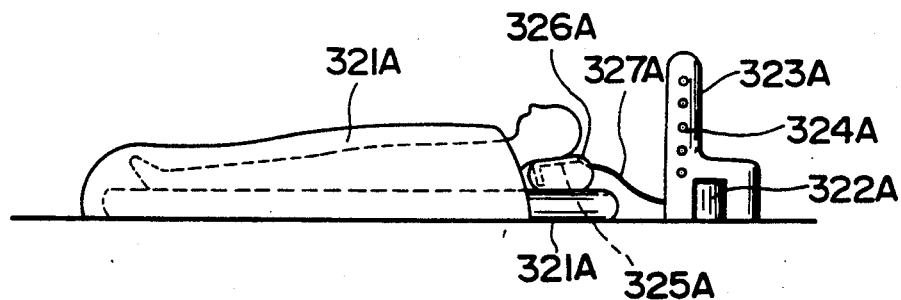
FIG. 55 is a side elevational view of a slightly different form of the apparatus according to this invention.
Figure 56:
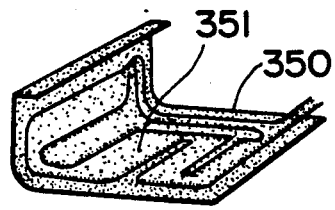
FIG. 56 is a perspective view of a cooling member which can be used in the embodiment of FIG. 55.

FIG. 55 shows substantially the same embodiment of FIGS. 52 and 53 in which similar parts are indicated by similar numerals affixed with alphabet A. In this embodiment, however, the cooling element or evaporator 325A mounted in the pillow 326A comprises a cooling plate 350 of thinner sheet material having a coolant passage 351 formed therein as shown in FIG. 56. This cooling element provides a sound like the murmur of a brook which is produced when the coolant from the condenser 324A is evaporated at the evaporator 352A. A person 320A lying on the mattress 321A can be cooled at his head by the cooling element 325A and at the same time mentally calmed by the sound from the interior of the pillow 326A.

Figure 57:
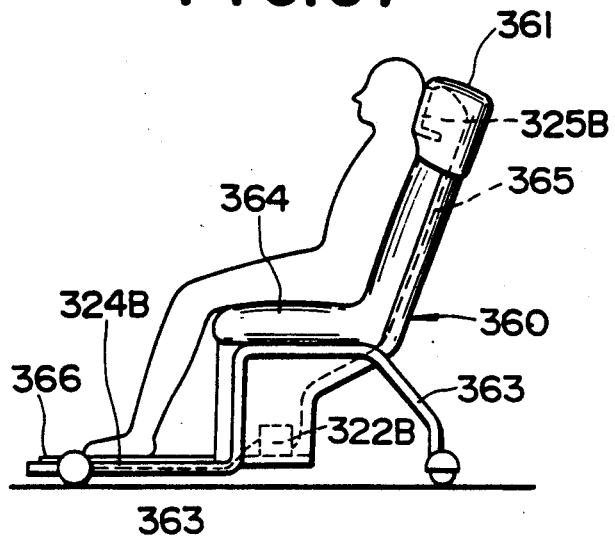
FIG. 57 is a side elevational view of a chair to which the concept of FIGS. 55 and 56 is applied.

FIG. 57 shows another embodiment of this invention in which the concept of FIGS. 55 and 56 is applied to a chair 360. The chair 360 comprises a head rest 361 into which substantially the same cooling element 325B as that of the embodiment shown in FIGS. 55 and 56 is assembled, a housing 362 located between legs 363 of the chair 360 below the seat 364 thereof and receiving a compressor 322B which is connected to the cooling element 325B in the head rest 361 through a pipe 365, and a foot rest 366 extending outwardly from the forward legs 363 and receiving a condenser 324B which is connected to the compressor 322B.

Figure 58:
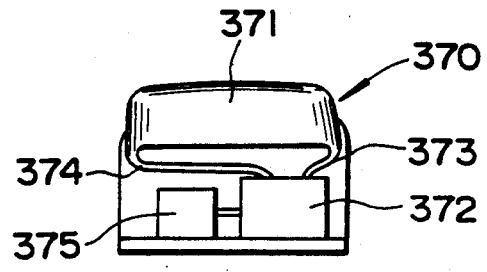
FIG. 58 is a front elevational view of a pillow to which the concept of FIGS. 55 and 56 is applied.

FIG. 58 shows another embodiment of this invention in which a pillow 370 comprises a head-engaging hollow portion 371 exposed outside thereof, a pump 372 mounted in the pillow 370 and connected to the hollow portion 371 through pipe portions 373 and 374, and a motor 375 disposed in the pillow 370 for driving the pump 372. In this embodiment, liquid such as water is circulated from the pump 374 to the hollow portion 371 through the pipe portions 373 and 374 so that a person using this pillow 370 will be cooled at his head by water and at the same time mentally calmed by a sound like the murmur of a brook which is produced when the water is circulated in the pillow 370.

Figure 59:
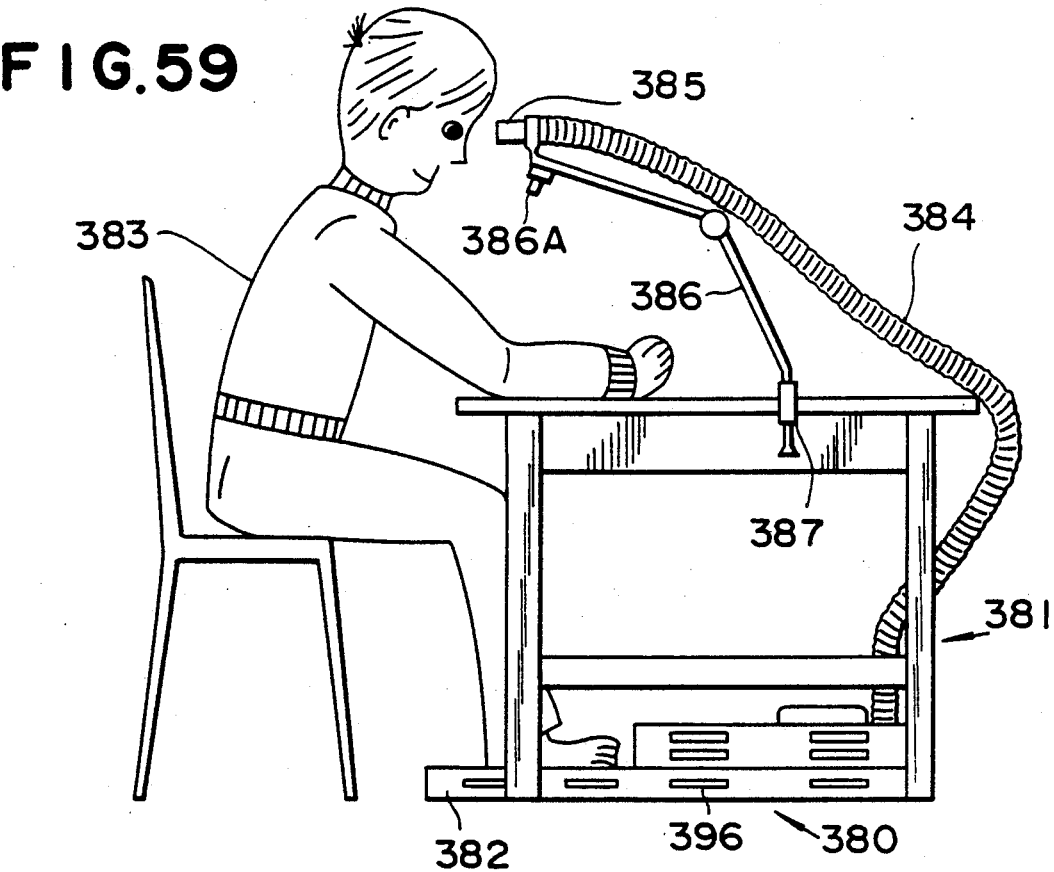
FIG. 59 is a side elevational view of further embodiment used for a person sitting at a desk.
Figure 60:
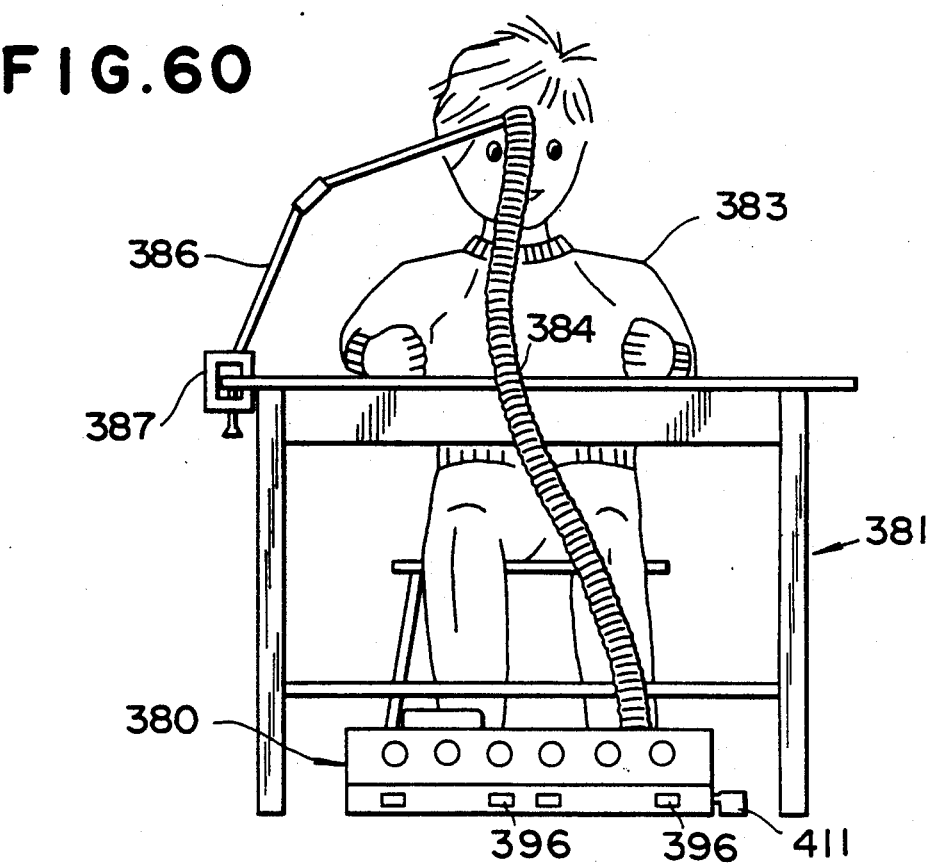
FIG. 60 is a front elevational view of FIG. 59.

FIGS. 59 and 60 show a further embodiment of this invention which is applied to a person sitting at a desk. In this embodiment, a cooling and warming apparatus 380 is placed below a desk 381 and comprises a foot-rest portion 382 on which the feet of a person 383 sitting at the desk 381 is placed, and a flexible hose 384 attached at one end to the body of the apparatus 380 and extending therefrom near the forehead of the person 383. The flexible hose 384 has a blowing nozzle 385 mounted on the outlet thereof and is supported in its operative position by means of an articulated support 386 which is mounted on the edge of the desk 381 by any suitable means such as vise 387. The support 386 includes a power switch 386A mounted thereon at the upper end.

The apparatus 380 comprises a base 390 having side and end walls 391 and 392 upstanding therearound. Each of the side walls 391 has a forward wall portion 394 and a rearward wall portion 395 which is higher than the forward wall portion. Each of the side and end walls 391 and 392 includes a plurality of vanes 396 extending outwardly and downwardly to form downwardly directed openings for conducting air from atmosphere to the interior of the apparatus 380.

The forward portion 390A of the base 390 includes a plurality of reinforcing members 397 (three shown in FIG. 61) which are attached to the inner surface of the forward portion 390A by any suitable means such as welding. The outermost members 397 include threaded holes 398 which correspond to apertures 399 formed in a foot-rest plate 400. Thus, the plate 400 can be mounted on the base 390 by means of screws (not shown) extending through the apertures 399 and screwed into the threaded holes 398 to close the forward portion 390A of the base 390. Between the foot-rest plate 400 and the reinforcing members 397 is mounted a heat-radiation pipe 401 which will be described in detail hereinafter.

The rearward portion 390B of the base 390 includes stud bolts 402 disposed on the inner surface thereof adjacent to one side. These stud bolts 402 receive apertures 403 formed in a compressor base plate 404 on which a compressor 405 is mounted by any suitable manner. Nuts (not shown) are screwed on the portions of the stud bolts 402 extending through the apertures 403 of the base plate 404 for mounting the compressor 405 on the base 390.

The rearward portion 390B also includes a cooling box 406 mounted on the inner surface thereof adjacent to the opposite side by any suitable manner. The cooling box 406 is made of any thermally insulating material such as foamed styrene and receives a cooling element 407 connected to the compressor 405 through a pipe 408. In such an arrangement, the heat-radiation pipe 401 and cooling plate 407 serve, respectively, as a condenser and evaporator as in the aforementioned cooling and warming device utilizing a coolant such as Freon. The cooling box 406 includes a drain pipe 410 attached thereto for removing droplets condensed on the surface of the cooling plate 407. The drain pipe 410 is received in a water receiver for accumulating the removed water which is disposed outside of the base 390.

The cooling box 406 includes a relatively large opening 412 formed in the rearward wall thereof. A blower 413 of Silocco type is disposed between the rearward wall of the cooling box 406 and the rearward end wall of the base 390 with the inlet 414 thereof connected to the opening 412 of the cooling box 406.

Figure 66:
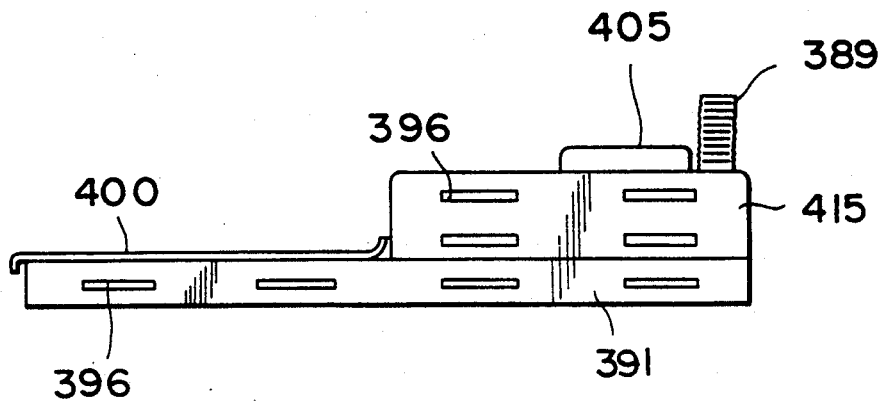
FIG. 66 is a side elevational view of the embodiment of FIG. 61.

The rearward portion 390B of the base 390 is closed by a covering 415 having a plurality of vanes 416 similar to those of the base 390. The covering 415 includes an opening 417 formed therein at the top from which the head of the compressor 405 extends outwardly when the covering 415 is mounted on the base 390. The covering 415 also includes a relatively small opening 418 formed therein at the top through which the flexible hose 384 (FIGS. 59 and 66) extends into the base 390 and is connected with the outlet 419 of the blower 413.

When the compressor 405 is driven by any suitable means such as an electric motor housed therein, the foot-rest plate 400 is warmed by the heat-radiation pipe 401 while the forehead of the person 383 (FIGS. 59 and 60) is cooled by air which is cooled at the cooling plate 407 and supplied therefrom by the blower 413 through the flexible pipe 384 for blowing against the forehead of the person.

FIG. 67 shows one form of a nozzle which can be used in the embodiment shown in FIGS. 59 to 66. In this form, a nozzle 420 has a barrel-shape and is connected with the outlet of the flexible hose 384. The nozzle 420 includes a filter 421 mounted therein at the outlet thereof. FIG. 68 shows another form of similar nozzle in which a nozzle 422 has an arcuate outlet 423.

Figure 61:
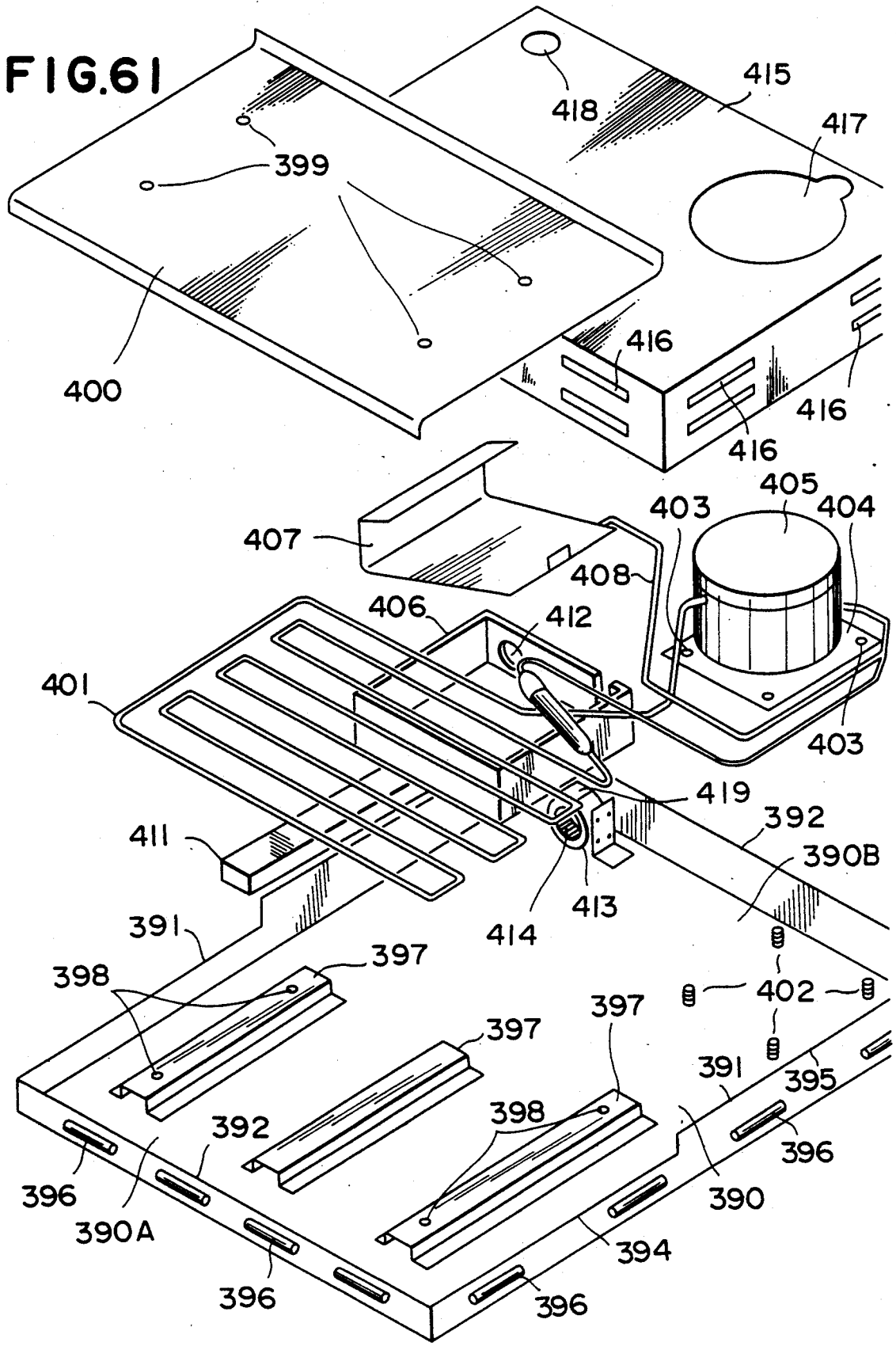
FIG. 61 is an exploded, perspective view of the embodiment shown in FIGS. 59 and 60.
Figure 62:
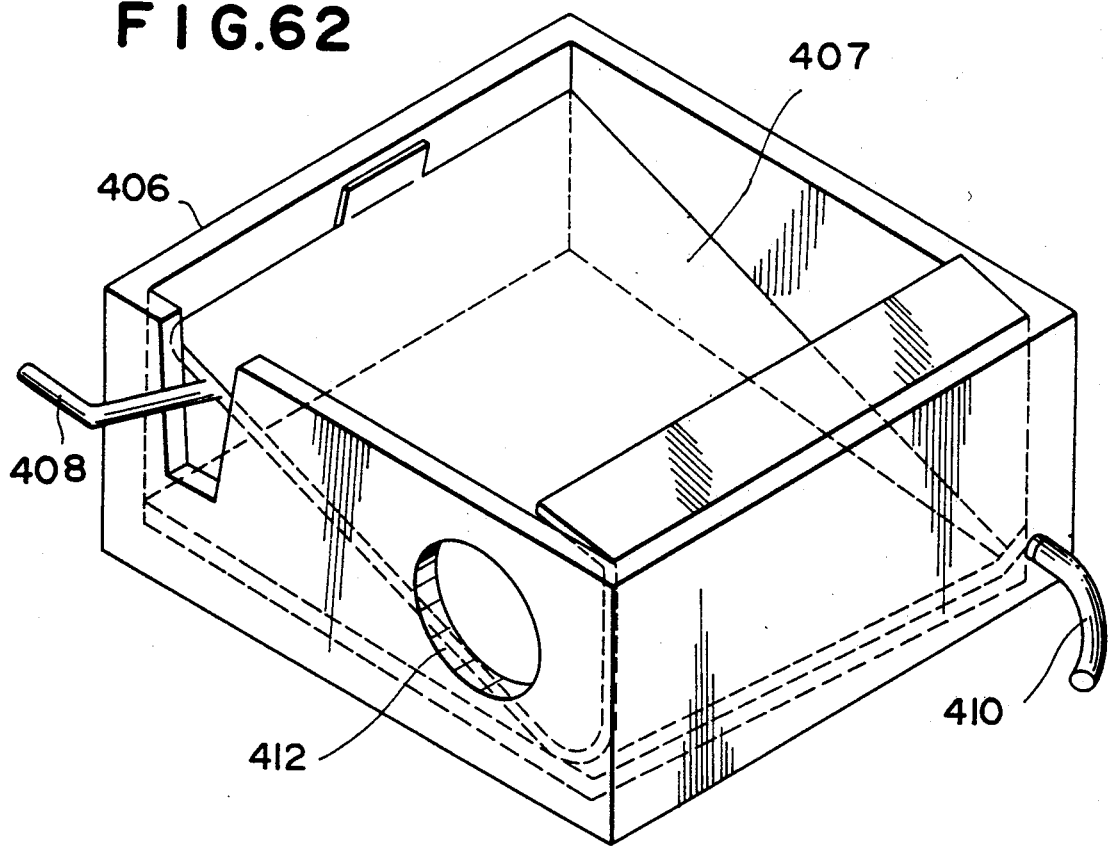
FIG. 62 is a perspective view of the cooling box shown in FIG. 61.
Figure 63:
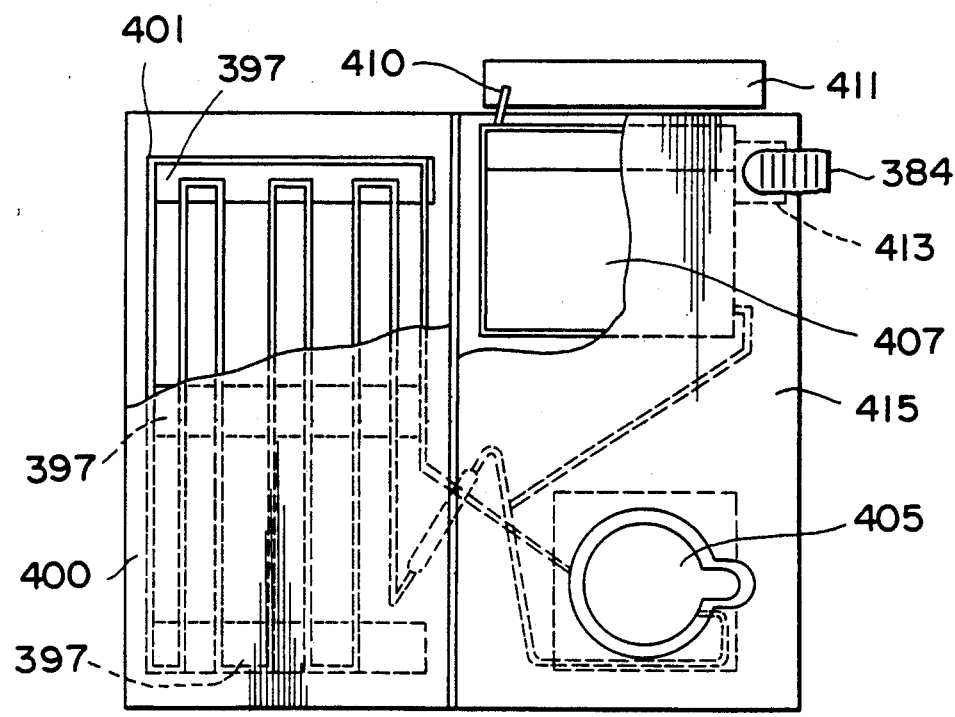
FIG. 63 is a top view, partially broken away, of the embodiment of FIG. 61.
Figure 64:
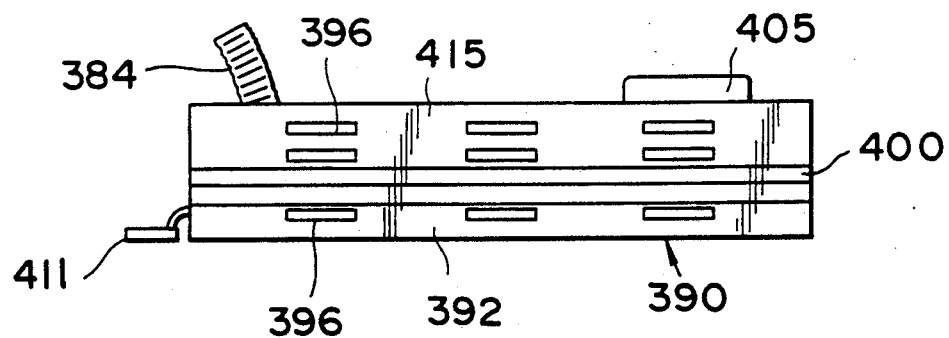
FIG. 64 is a front elevational view of the embodiment of FIG. 61.
Figure 65:
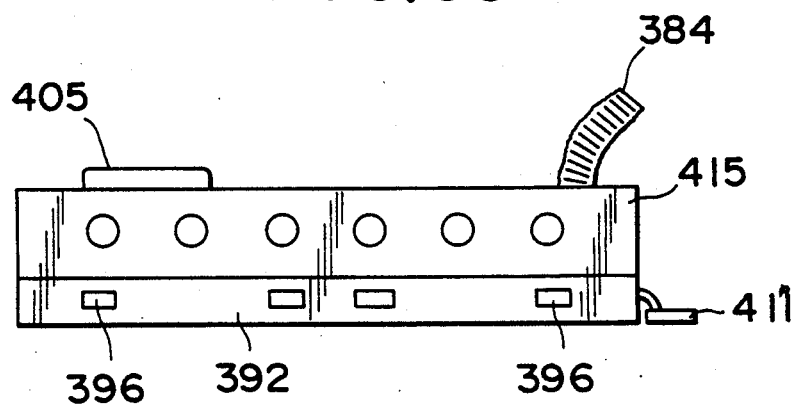
FIG. 65 is a back view of the embodiment shown in FIG. 61.

FIG. 69 shows another form of the cooled-air supplying means which can be used in place of the cooling box 406 and blower 413 shown in FIGS. 61 and 62. This comprises a cylindrical hollow casing 430 having its outward periphery which is covered by any thermally insulating material 431. Within the casing 430 is disposed a coiled cooling pipe 432 similar to the cooling plate 407 shown in FIGS. 61 and 62. The cooling pipe 432 includes an inlet and outlet 433, 434 which extend outwardly through the wall of the casing 430 for connecting to the compressor 405 shown in FIGS. 61 and 63.

A fan device 435 is mounted on the casing 430 at the rearward opened end thereof. The fan device 435 is in the form of a cylindrical hollow tube in which a fan 436 is coaxially disposed and connected with an electric motor 437 which is supported by means of rods 438 in the tube. Apparently, when the fan 436 is driven by the electric motor 437, air is fed from atmosphere through the casing 430 to the flexible hose 384. The air is cooled at the coiled cooling pipe 432 and then conducted into the flexible hose 382.

Figure 70:
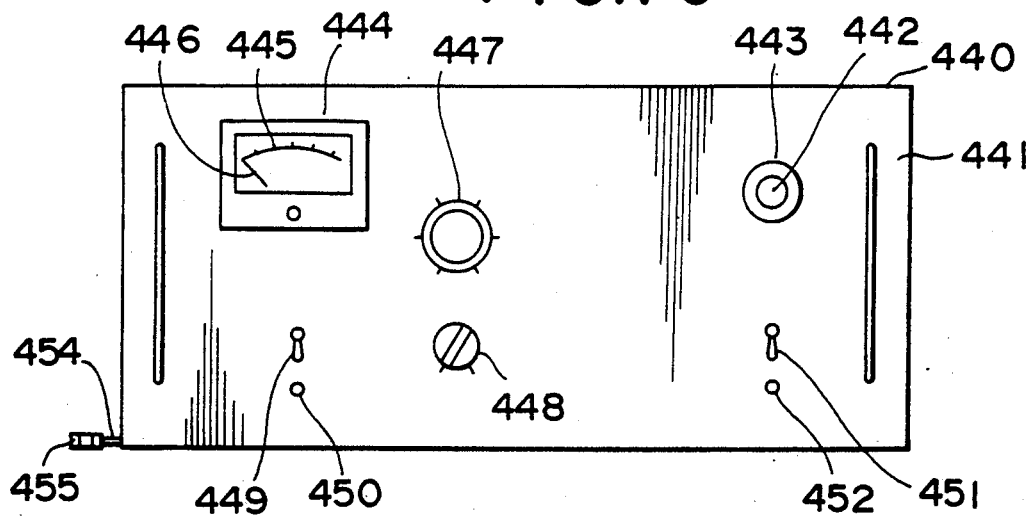
FIG. 70 is a front elevational view of an apparatus for measuring the brain power of a person which is increased in brain activity by means of the apparatus of this invention which can be in the form of the respective embodiment shown in the previous figures.
Figure 71:
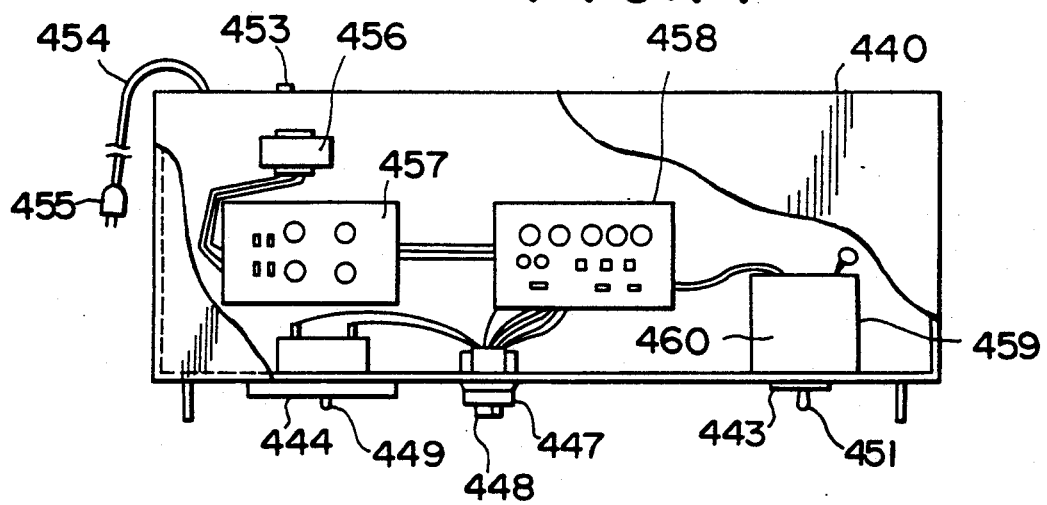
FIG. 71 is a top view, partially broken away, of the measuring apparatus shown in FIG. 70.

This invention provides also an apparatus for measuring the brain power of a person which is increased in brain activity by use of such a cooling and warming apparatus as in the previously mentioned embodiments. Referring to FIGS. 70 and 71, such a measuring apparatus comprises a housing 440 and a forward panel 441. The forward panel 441 includes a finger-inserting opening 442 formed therethrough the edge of which is covered by a protective ring 443. On the forward panel 441 are mounted a meter 444 having a scale 445 and an indicator 446, an knob 447 for roughly adjusting the indication of the indicator 446 on the scale 445, another knob 448 for accurately adjusting the above indication, a power switch 449, a display lamp 450 indication power-on, a switch 451 for controlling a source of light and a display lamp 452 for indicating light-on. Within the housing 440 are mounted a fuse 453 for the power source, a power line 454 and an attaching plug 455.

Within the housing 440 are also mounted a power transformer 456, a rectifier 457, an amplifier 458 and a measuring section 459.

Figure 72:
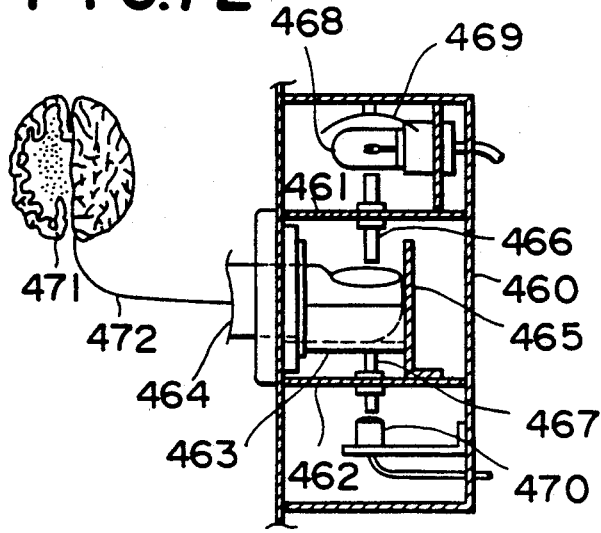
FIG. 72 is a cross-sectional view showing the section for receiving the finger of a person to be measured in brain power.
Figure 73:
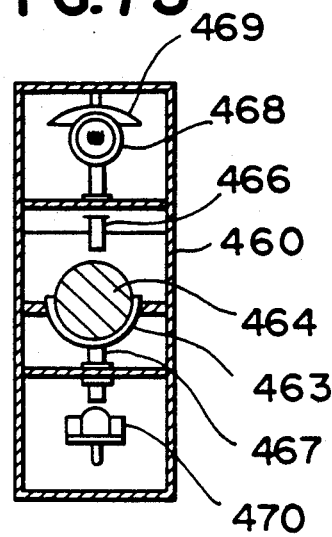
FIG. 73 is a view similar to FIG. 72, showing the finger-receiving section as viewed from another direction.

The measuring section 459 includes a housing 460 located behind the finger-inserting opening 442 of the panel 441. Refferring to FIGS. 72 and 73, the housing 460 includes upper and lower beams 461 and 462 disposed thereacross back and forth. The lower beam 462 supports a trough-like finger receiver 463 for holding a finger 464 inserted thereinto through the opening 442 in a horizontal position. The lower beam 462 also supports a stopper 465 for positioning the finger 464 at a predetermined location in the finger receiver 463.

The upper beam 461 supports a transparent rod 466 of acryl disposed verticaly. The lower beam 462 also supports a similar transparent rod 467 which is vertically located in alignment with the upper rod 466 on the upper beam 461. A lamp 468 is mounted on the housing 460 above the upper transparent rod 466 for forming a source of light. Above the lamp 468 is mounted a reflector 469 on the top wall of the housing 460. A photoreceptor 470 is mounted on the housing 460 adjacent to the lower end of the lower transparent rod 467.

When the finger 464 is in the finger receiver 463 and the lamp 468 is turned on, light is transmitted from the upper end of the upper transparent rod 466 to the lower end thereof. Light radiated from the lower end of the rod 466 is transmitted through the positioned finger 464 to the upper end of the lower transparent rod 467. The light passes through the rod 467 to the lower end thereof and then is received by the photoreceptor 470. In this connection, the blood pipe in the finger 464 is connected to the brain 471 through blood pipe 472. Therefore, if the flow of blood in the brain 471 is changed for any reason, the flow of blood in the finger 464 also is correspondingly changed. Thus, the brain activity can be measured by measuring the flow of blood in the finger 464 which will appear at the photoreceptor 470 as any change of photocurrent.

It is desirable that the upper and lower ends of the lower rod 467 are respectively disposed adjacent to the finger 463 and photoreceptor 470 as close as possible. Alternatively, optical fibers are used in place of the acryl rods. Further, the inner walls of the housing 460 are preferably black-colored for preventing any reflection of light.

Figures 74, 75:
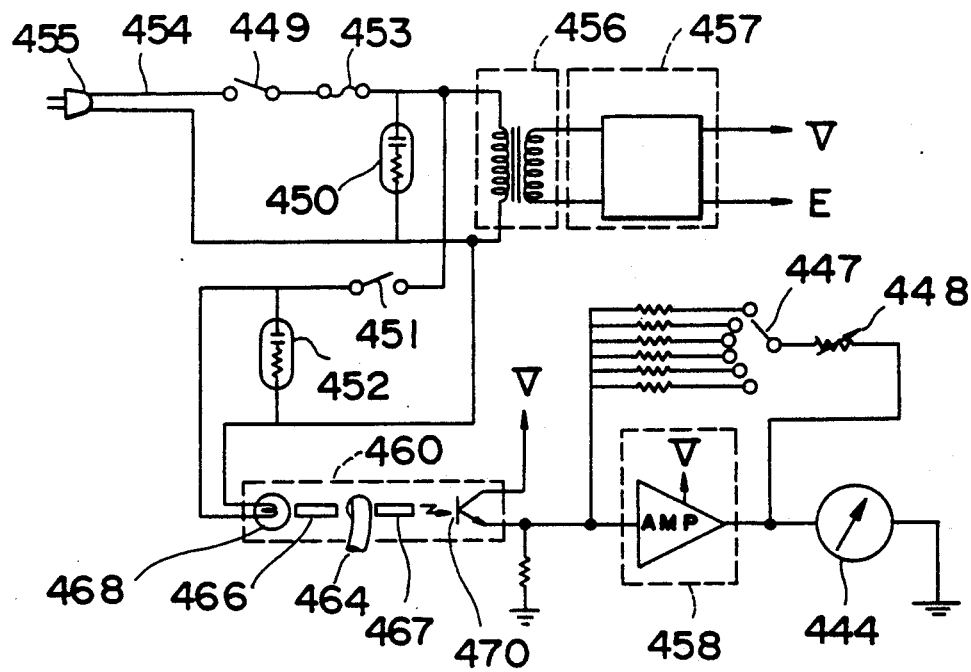
FIG. 74 is a circuit diagram of the embodiment shown in FIGS. 70 to 73.
FIG. 75 is a view of a performance test paper which is used for confirming the operation of the measuring apparatus.

FIG. 74 shows a diagram of a circuit which can be used in the apparatus shown in FIGS. 70 to 73.

In use, the power switch 449 is first turned on. Next, the finger 464 is inserted into the receiver 463 through the opening 442 with the pawl 464 directed upwardly. If the tip of the finger 464 engages with the stopper 465, it will be positioned in place. Thereafter, the light switch 451 is turned on and then the adjusting knobs 447 and 448 are manually operated to obtain zero indication or any other indication of the indicator 446 in the meter 444. The finger 464 is then rotated around its central axis to obtain a position of the indicator 446 that minimum value is pointed out. If the indicator 446 is moved beyond the maximum value of the scale 445 at this time point, it is necessary to return the indicator 446 within the scope of the scale 445 by adjusting the knobs 447 and 448. Thereafter, the light switch 451 is turned off and the finger 464 is drawn out through the opening 442. Subsequently, the person having the finger 464 is subjected to the operation of the apparatus for increasing the brain activity as in the previously mentioned embodiments. Thereafter, the finger 464 is again inserted into the finger receiver 463 and the light switch 451 is turned on to measure a measurement in the meter 444 without movement of the adjusting knobs 447 and 448. This measurement is compared with the measurement prior to being subjected to the operation of the apparatus for increasing the brain power.

The increase of brain power by use of the brain-activity increasing apparatus of this invention is thus measured by the measuring apparatus of this invention. The so obtained measurements have been compared with measurements obtained by using a performance test paper shown in FIG. 75. This paper has four steps of randomly arranged figures, each step consisting of two lines each of which has sixty-three figures. In use, the sum of two digits obtained by multiplying each adjacent figures in each line in one times another is written between the adjacent figures above that line. For example, a first line in a first step is calculated as follows:

$$3 \times 4 = 12, 1+2=3;$$

$$4 \times 5 = 20, 2+0=2;$$

$$5 \times 9 = 45, 4+5=9;$$

The so obtained figures 3, 2, 9 ..., which are underlined, are written between each adjacent figures above the first line of the first step. This calculation is repeated for each line of each step. After two minutes elapse, the calculation is changed from a particular step to next step. When all the steps have been calculated, proper and wrong figures which have been written in the test paper are counted. The proper figures are used to estimate a performance of operation for a particular tested person. Examples in which some persons have been tested both by the measuring apparatus of this invention and the above performance test paper will be described below.

EXAMPLE 1

A student, Kazuo Koga was tested.

(a) The performance test paper: Before use of the brain-activity increasing apparatus of this invention;
proper figures 303
wrong figures 3.
After use of the brain-activity increasing apparatus of this invention;
proper figures 392
wrong figures 3.

This result indicates that his brain power has been increased up to 29% by use of the brain-activity increasing apparatus of this invention.

(b) The measuring apparatus of this invention: Before use of the brain-activity increasing apparatus of this invention; value indicated on the meter 444 was 24. After use of the brain-activity increasing apparatus of this invention; value indicated on the meter was 31.

This result indicates that he has been increased in brain power up to 29.1% which substantially corresponds to the result from the performance test paper.

EXAMPLE 2

A student, Masami Suga was tested.

(a) The performance test paper: Before use of the brain-activity increasing apparatus of this invention;
proper figures 249
wrong figures 10.
After use of the brain-activity increasing apparatus of this invention;
proper figures 309
wrong figures 4.

This result indicates that he has been improved up to 24% in his operation and upto 60% in rate of proper figures.

(b) The measuring apparatus of this invention: Before use of the brain-activity increasing apparatus of this invention; value indicated on the meter 444 was 33. After use of the brain-activity increasing apparatus of this invention; value indicated on the meter was 43.

This result indicates that he has been increased in his brain power up to 30% which substantially corresponds to the result from the performance test paper.

EXAMPLE 3

Masami Suga was again tested immediately after the example 2.

(a) The performance test paper: Before use of the brain-activity increasing apparatus of this invention;

proper figures 151
wrong figures 7.

After use of the brain-activity increasing apparatus of this invention;
proper figures 182
wrong figures 2.

This result indicates that he has been improved upto 20% in his operation and upto 71% in rate of proper figures.

(b) The measuring apparatus of this invention: Before use of the brain-activity increasing apparatus of this invention; value indicated on the meter was 9.5. After use of the brain-activity increasing apparatus of this invention; value indicated on the meter was 16.

This result indicates that he has been increased up to 68.4% in his brain power which substantially corresponds to the result from the performance test paper.

I claim:

1. An apparatus for effecting a physiological change in a person's body comprising a chair having a head rest and a foot rest, a cooling means mounted in said head rest of said chair for cooling the head of a person seated in said chair by direct contact of the head of the person with said head rest, and warming means mounted in said foot rest of said chair for simultaneously warming the soles of the feet of said person sitting in said chair by direct contact of the feet of said person with said foot rest.

2. An apparatus as defined in claim 1, wherein said cooling means comprises a compressor for compressing a coolant, and said warming means comprising a condenser connected with said compressor for receiving the compressed coolant, said cooling means further comprising an evaporator connected with said condenser through a capillary pipe for evaporating the coolant from said condenser and further connected with said compressor for returning the evaporated coolant back thereto.

3. An apparatus as defined in claim 2, wherein said chair further includes a base and said compressor is disposed in said base of said chair, said evaporator being located in the head rest of said chair, and said condenser being positioned in the foot rest of said chair.

4. An apparatus as defined in claim 2, wherein said condenser is located in the foot rest of said chair, said compressor and evaporator being disposed within the base of said chair and wherein a blower means is connected with said evaporator for blowing air cooled at said evaporator toward the head of said person sitting on said chair.

5. An apparatus as defined in claim 2, wherein said evaporator comprises an exposed portion in said head rest for direct contact with the head of a person seated in the chair.

6. An apparatus as defined in claim 2, wherein said condenser comprises a zigzagged condenser pipe disposed in said foot rest.

7. An apparatus as defined in claim 1, wherein said cooling means and said warming means are in the form of an electronic device utilizing the Peltier effect, said electronic device comprising a thermoelement having a cold section located at the head rest of said chair and a hot section disposed at the foot rest of said chair.

8. An apparatus as defined in claim 1, wherein said foot rest further comprises a plurality of small openings for permitting upward movement of air warmed by said warming means for warming the soles of the feet of a person seated in said chair.

9. An apparatus as defined in claim 1, wherein said chair includes a base, said warming means comprises a compressor for compressing a coolant mounted on said foot rest of said chair beneath said base of said chair, and said chair further includes side vents located above said base of said chair for causing air heated by said compressor to escape to the atmosphere.

10. Apparatus for effecting a physiological change in a person's body comprising a chair having a base, a seat overlying said base, a back rest mounted on said base and extending upwardly from said base, a head rest on said back rest, cooling means mounted in said head rest for cooling the head of a person seated in said seat by direct contact of the head of the person with said head rest, a foot rest mounted on said base and extending from said base, warming means mounted in said foot rest for simultaneously warming the feet of a person sitting in said chair by direct contact of the feet of said person with said foot rest, source means in said base underlying said seat, first connecting means in said base and in said back rest and extending between said cooling means and said source means for providing a source of cooling to said cooling means, and second connecting means in said base extending between said heating means and said source means providing a source of heating to said heating means, whereby a person's head is cooled while such person's feet are simultaneously warmed while sitting in said chair.

* * * * *